(12) United States Patent
Wu et al.

(10) Patent No.: US 11,298,536 B2
(45) Date of Patent: Apr. 12, 2022

(54) ELECTRICAL-STIMULATION DEVICE AND OPERATION METHOD THEREOF AND ELECTRICAL-STIMULATION SYSTEM

(71) Applicant: GIMER MEDICAL. Co. LTD., New Taipei (TW)

(72) Inventors: Chen-Tun Wu, New Taipei (TW); Jian-Hao Pan, New Taipei (TW)

(73) Assignee: GIMER MEDICAL. CO. LTD., New Taipei (TW)

( * ) Notice: Subject to any disclaimer, the term of this patent is extended or adjusted under 35 U.S.C. 154(b) by 0 days.

(21) Appl. No.: 16/884,968

(22) Filed: May 27, 2020

(65) Prior Publication Data
US 2020/0376267 A1 Dec. 3, 2020

(30) Foreign Application Priority Data
May 31, 2019 (CN) .......................... 201910468697.8

(51) Int. Cl.
*A61N 1/36* (2006.01)
*A61N 1/04* (2006.01)

(52) U.S. Cl.
CPC ....... *A61N 1/36034* (2017.08); *A61N 1/0476* (2013.01)

(58) Field of Classification Search
CPC ................ A61N 1/0476; A61N 1/3752; A61N 1/36034; A61N 1/05; A61N 1/36; A61N 1/36062; A61N 1/3605; A61N 1/36125
See application file for complete search history.

(56) References Cited

U.S. PATENT DOCUMENTS

| 4,898,173 A * | 2/1990 | Daglow ............... A61N 1/3752 439/585 |
| 2009/0234411 A1 | 9/2009 | Sambelashvili et al. |

(Continued)

FOREIGN PATENT DOCUMENTS

| CN | 106606820 A | 5/2017 |
| TW | 201700125 A | 1/2017 |

OTHER PUBLICATIONS

Extended European Search Report for European Application No. 20177148.2, dated Oct. 5, 2020.

(Continued)

*Primary Examiner* — Carl H Layno
*Assistant Examiner* — Anh-Khoa N Dinh
(74) *Attorney, Agent, or Firm* — Birch, Stewart, Kolasch & Birch, LLP

(57) ABSTRACT

An electrical-stimulation device includes an electrical-stimulation signal-generating circuit, a first connection unit, a first conductive member and a second conductive member. The electrical-stimulation signal-generating circuit has a first channel for providing a first electrical-stimulation signal. The first connection unit has a plurality of first contact points and a plurality of second contact points, wherein the first contact points and the second contact points are alternately arranged. The first conductive member is connected to the first contact points. The second conductive member is connected to the second contact points. The first conductive member and the second conductive member are electrically connected to the first channel, so that the first electrical-stimulation signal is transmitted through the first contact points and the second contact points corresponding to the first channel.

19 Claims, 16 Drawing Sheets

(56) References Cited

U.S. PATENT DOCUMENTS

| | | | |
|---|---|---|---|
| 2012/0071948 A1* | 3/2012 | Pianca | A61N 1/3752 |
| | | | 607/46 |
| 2012/0078327 A1 | 3/2012 | Sloan et al. | |
| 2014/0002318 A1 | 1/2014 | Meulmester et al. | |
| 2018/0050189 A1 | 2/2018 | Rump et al. | |
| 2018/0064945 A1* | 3/2018 | Parker | A61N 1/3787 |

OTHER PUBLICATIONS

Taiwanese Office Action and Search Report for Taiwanese Application No. 110118255, dated Jun. 23, 2021.

* cited by examiner providing a lead for electrically connecting the first connection unit — S1202

FIG. 12 providing a lead for electrically connecting the first connection unit — S1302

FIG. 13 providing a first lead for electrically connecting the first connection unit — S1402

↓ providing a second lead for electrically connecting the second connection unit — S1404

FIG. 14

ELECTRICAL-STIMULATION DEVICE AND OPERATION METHOD THEREOF AND ELECTRICAL-STIMULATION SYSTEM

CROSS REFERENCE TO RELATED APPLICATIONS

This application claims priority of China Patent Application No. 201910468697.8, filed on May 31, 2019, the entirety of which is incorporated by reference herein.

TECHNICAL FIELD

The disclosure relates to an electrical-stimulation device, and in particular it relates to an electrical-stimulation device and an operation method thereof and an electrical-stimulation system.

BACKGROUND

In recent years, dozens of therapeutic nerve electrical-stimulation devices have been developed, and at least tens of thousands of people undergo electrical-stimulation device implantation every year. Due to the development of precision manufacturing technology, the size of medical device has been miniaturized and may be implanted inside the human body, for example, an implantable electrical-stimulation device.

However, in the current implantable electrical-stimulation device, due to miniaturization or component matching, the number of channels of the circuit of the electrical-stimulation device for providing electrical-stimulation signals is limited, so that the number of contact points of the connection unit of the electrical-stimulation device may not correspond to the number of channels of the electrical-stimulation device. Therefore, how to effectively make the number of contact points of the connection unit of the electrical-stimulation device corresponds to the number of channel of the electrical-stimulation device to increase the flexibility of component use has become an important issue.

SUMMARY

The disclosure provides an electrical-stimulation device and an operation method thereof and an electrical-stimulation system, so that the number of contact points of the connection unit may corresponds to the number of channels of the electrical-stimulation device for providing an electrical-stimulation signal, thereby increasing the flexibility of the connection unit for use.

The disclosure provides an electrical-stimulation device, which includes an electrical-stimulation signal-generating circuit, a first connection unit, a first conductive member and a second conductive member. The electrical-stimulation signal-generating circuit has a first channel for providing a first electrical-stimulation signal. The first connection unit has a plurality of first contact points and a plurality of second contact points, wherein the first contact points and the second contact points are alternately arranged. The first conductive member is connected to the first contact points. The second conductive member, connected to the second contact points. The first conductive member and the second conductive member are electrically connected to the first channel, so that the first electrical-stimulation signal is transmitted through the first contact points and the second contact points corresponding to the first channel.

The disclosure provides an electrical-stimulation system, which includes at least one lead and an electrical-stimulation device. The electrical-stimulation device is electrically connected to the aforementioned lead. The electrical-stimulation device includes an electrical-stimulation signal-generating circuit, a first connection unit, a first conductive member and a second conductive member. The electrical-stimulation signal-generating circuit has a first channel for providing a first electrical-stimulation signal. The first connection unit has a plurality of first contact points and a plurality of second contact points, wherein the first contact points and the second contact points are alternately arranged. The first conductive member is connected to the first contact points. The second conductive member is connected to the second contact points. The first conductive member and the second conductive member are electrically connected to the first channel, so that the first electrical-stimulation signal is transmitted through the first contact points and the second contact points corresponding to the first channel.

The disclosure provides an operation method of an electrical-stimulation device, which includes the following steps. A first electrical-stimulation signal is provided by the first channel of an electrical-stimulation signal-generating circuit. A first connection unit is provided, wherein the first connection unit has a plurality of first contact points and a plurality of second contact points, and the first contact points and the second contact points are alternately arranged. A first conductive member is used to connect to the first contact points. A second conductive member is used to connect to the second contact points. The first conductive member and the second conductive member are electrically connecting to the first channel. The first electrical-stimulation signal is transmitted through the first contact points and the second contact points corresponding to the first channel.

According to the electrical-stimulation device and the operation method thereof and the electrical-stimulation system disclosed by the disclosure, at least two of the contact points of the connection unit are connected through the conductive member resulted in the same electrical polarity to reduce the corresponding needed number of channels of the electrical-stimulation signal-generating circuit for providing the electrical-stimulation signal and reduce the needed number of feedthroughs for connection between the channel and the contact points. The electrical-stimulation signal provided by the channel of the electrical-stimulation signal-generating circuit may be transmitted through the corresponding contact points. Moreover, the size of the electrical-stimulation device can be reduced owing to the reduced number of channel of the electrical-stimulation signal-generating circuit or the reduced number of feedthroughs for connection between the channel and the contact points. Therefore, even if the number of contact points of the connection unit and the number of channel are different, the connection unit and the channel may still corresponded to each other by the conductive member, thereby effectively increasing the flexibility of the connection unit for use. On the other side, it's much easier for clinician to use or setup the device/system. When the system is on, the polarities of the contact points are determined, thus the polarities of electrodes of the lead are determined to be interleaved, which can reduce the device/system setup time.

BRIEF DESCRIPTION OF DRAWINGS

The disclosure can be more fully understood by reading the subsequent detailed description and examples with references made to the accompanying drawings, wherein:

FIG. 12 is a flowchart of an operation method of an electrical-stimulation system according to an embodiment of the disclosure.

FIG. 13 is a flowchart of an operation method of an electrical-stimulation system according to another embodiment of the disclosure.

FIG. 14 is a flowchart of an operation method of an electrical-stimulation system according to another embodiment of the disclosure.

DETAILED DESCRIPTION OF DISCLOSED EMBODIMENTS

Technical terms of the disclosure are based on general definition in the technical field of the disclosure. If the disclosure describes or explains one or some terms, definition of the terms is based on the description or explanation of the disclosure. Each of the disclosed embodiments has one or more technical features. In possible implementation, a person skilled in the art would selectively implement all or some technical features of any embodiment of the disclosure or selectively combine all or some technical features of the embodiments of the disclosure.

In each of the following embodiments, the same reference number represents the same or a similar element or component.

Figure 1:
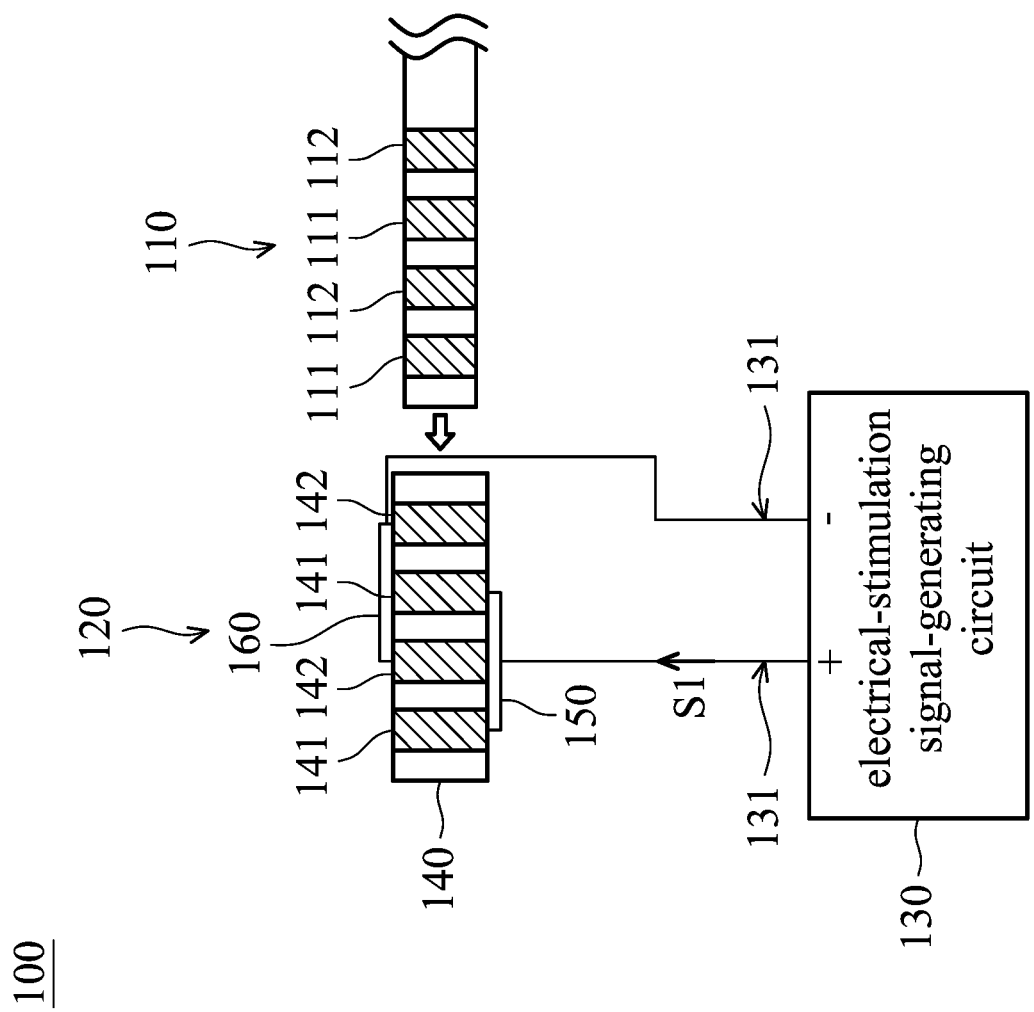
FIG. 1 is a schematic view of an electrical-stimulation system according to an embodiment of the disclosure.

FIG. 1 is a schematic view of an electrical-stimulation system according to an embodiment of the disclosure. Please refer to FIG. 1. The electrical-stimulation system 100 includes a lead 110 and an electrical-stimulation device 120. The lead 110 includes a plurality of first electrodes 111 and a plurality of second electrodes 112, wherein the first electrodes 111 and the second electrodes 112 are alternately arranged. In the embodiment, the distance between the first electrode 111 and the second electrode 112 which are adjacent to each other is, for example, between 1 mm and 8 mm.

The electrical-stimulation device can be an implanted device (with or without battery), an external stimulator (with lead implanted inside the body) or a transcutaneous electrical-stimulation device (TENS). The electrical-stimulation device 120 is electrically connected to the lead 110. The electrical-stimulation device 120 includes an electrical-stimulation signal-generating circuit 130, a first connection unit 140, a first conductive member 150 and a second conductive member 160. The electrical-stimulation signal-generating circuit 130 has a first channel 131 for providing a first electrical-stimulation signal S1. Here, a "channel" is defined as at least two electrodes that receive a specified pattern (such as pulse width, amplitude, pulse frequency, intra-pulse frequency, duration, duty cycle) or sequence of stimulus pulses. Thus, where more than one "channel" is available, each channel may be programmed to provide its own specified pattern or sequence of stimulus pulses to its corresponding electrodes. In operation, all of the stimulus patterns applied through all of the channels of such multi-channel system thus combine to provide an overall stimulation pattern.

The first connection unit 140 has a plurality of first contact points 141 and a plurality of second contact points 142, wherein the first contact points 141 and the second contact points 142 are alternately arranged. In this case, there are two first contact points 141 and two second contact points 142 in the first connection unit 140. In addition, the first contact points 141 of the first connection unit 140 may be correspondingly electrically connected to the first electrodes 111 of the lead, respectively. The second contact points 142 of the first connection unit 140 may be correspondingly electrically connected to the second electrodes 112 of the lead, respectively. Therefore, the electrical polarities of first contact points 141 and the second contact points 142 are corresponding to the electrical polarities of the first electrodes 111 and the second electrodes 112, respectively. Furthermore, the total number of first contact points 141 corresponds to (equals to) a total number of first electrodes 111, and a total number of second contact points 142 corresponds to a total number of second contact points 112.

In the embodiment, the electrical polarities of the first contact points 141 and the second contact points 142 may be the same (i.e. when the electrical-stimulation signal is powered by a direct current source), or they may be opposite (i.e. when the electrical-stimulation signal is an biphasic alternating current (AC) signal or biphasic square signal). When the electrical polarities of the first contact points 141 and the second contact points 142 are opposite, such as the electrical polarities of the first contacts 141 are "positive" and the electrical polarities of the second contact points 142 are "negative", or the electrical polarities of the first contact points 141 are "negative" and the electrical polarities of the second contact points 142 are "positive". The electrical polarities of first contact points 141 (the same as the first electrodes 111) and the second contact points 142 (the same as the second electrodes 112) will be alternated or bipolar arranged, when the electrical stimulation signal is AC signal or biphasic signal.

The first conductive member 150 and the second conductive member 160 are metal or alloy conductors covered with an insulating material (such as Teflon), wherein the insulating material at two terminals of each first conductor 150 and each second conductor 160 is removed to be used to an electrical connection. The first conductive member 150 is connected to at least two first contact points 141. That is, the first conductive member 150 crosses over at least one second contact point 142 to connect together the first contact points 141 that are spaced apart. The second conductive member 160 is connected to at least two second contact points 142. That is, the second conductive member 160 crosses over at least one first contact point 141 to connect together the second contact points 142 that are spaced apart, together. The first conductive member 150 and the second conductive member 160 are electrically connected to the first channel 131 so that the first electrical-stimulation signal S1 is transmitted through the first contact points 141 and the second contact points 142 corresponding to the first channel 131.

The first electrical-stimulation signal S1 generated from the electrical stimulation signal generating circuit 130 transmitted by the first channel 131 will be conducted by different feedthroughs (f, will be described in FIG. 7B) of the electrical stimulation signal generating circuit 130, corresponding conductive elements to connect with the corresponding conductive members (150, 160) and the corresponding contact points (141, 142). Then the first electrical-stimulation signal S1 will be transmitted through the electrical polarity alternated first electrodes 111 and the second electrodes 112 of the lead 110. Two of the first contact points 141 are connected through the first conductive members 150 and two of the second contact points 142 are connected through the second conductive members 160, which resulted in the same electrical polarity of the two first electrodes 111 and the same electrical polarity of the two second electrodes 112. Thus, four electrodes (111, 112) only need one output channel 131 of the electrical-stimulation signal-generating circuit 130 to electrically connect to the first and second conductive members 150, 160. There is no need to use two channels to the control the parameters (such as pulse rate, pulse frequency and signal intensity) of the electrical-stimulation signal S1, which can reduce the needed number of feedthroughs for connection between the channel 131 and the contact points (141, 142) and reduce the needed number of channels. Therefore, four contact points on the connection unit may be adjusted to two electrical polarities, and corresponded to one first channel 131 of the electrical-stimulation signal-generating circuit 130, thereby increasing the flexibility of the connection unit for use. One feature of this embodiment is that the clinician need not select which electrodes of the lead are activated. Instead, the electrodes are all activated, and the clinician need not select which of the active electrode is negative polarity or positive polarity, either.

In the embodiment, a total number (two) of first conductive member 150 and the second conductive member is less than a total number (four) of first contact points 141 and the second contact points 142. In addition, the first electrical-stimulation signal S1 is, for example, a pulse alternating current signal having biphasic sine or square waveform and the pulse frequency range thereof is, for example, between 0 and 1 KHz. Furthermore, the intra-pulse frequency range of the first electrical-stimulation signal S1 is 100 KHz to 1000 KHz.

Furthermore, the electrical-stimulation system 100 of the embodiment may be a transcutaneous external stimulator or may be implanted inside the human body. When the electrical-stimulation system 100 is implanted inside the human body, the electrical-stimulation system 100 may be placed under the skin of the human body, and one terminal of the lead 110 is connected to the first connection unit 140, and the other terminal of the lead 110 is placed close to a target area to be stimulated. The electrical-stimulation system 100 as a spinal cord electrical-stimulation system is taken as an example, the other terminal of at least part of the lead is disposed in the epidural space to electrically stimulate the spinal cord, the spinal nerve or the dorsal root ganglia (DRG). The electrical-stimulation signal-generating circuit 130 of the electrical-stimulation system 100 transmits the first electrical-stimulation signal S1 to the electrode of the other terminal of the lead 110 through the lead 110, so as to electrically stimulate the target area. The current transmitted by the electrical-stimulation system 100 may flow out from the first contact points 141 of the lead 110, and then conduct through the human tissue, and then flow back to the lead 110 from the second contact points 142. In addition, the target nerve area of electrical stimulation may also be in the brain for electrical stimulation of brain cortex or deep brain stimulation (DBS) or abdominal and peripheral nerves.

Figure 2:
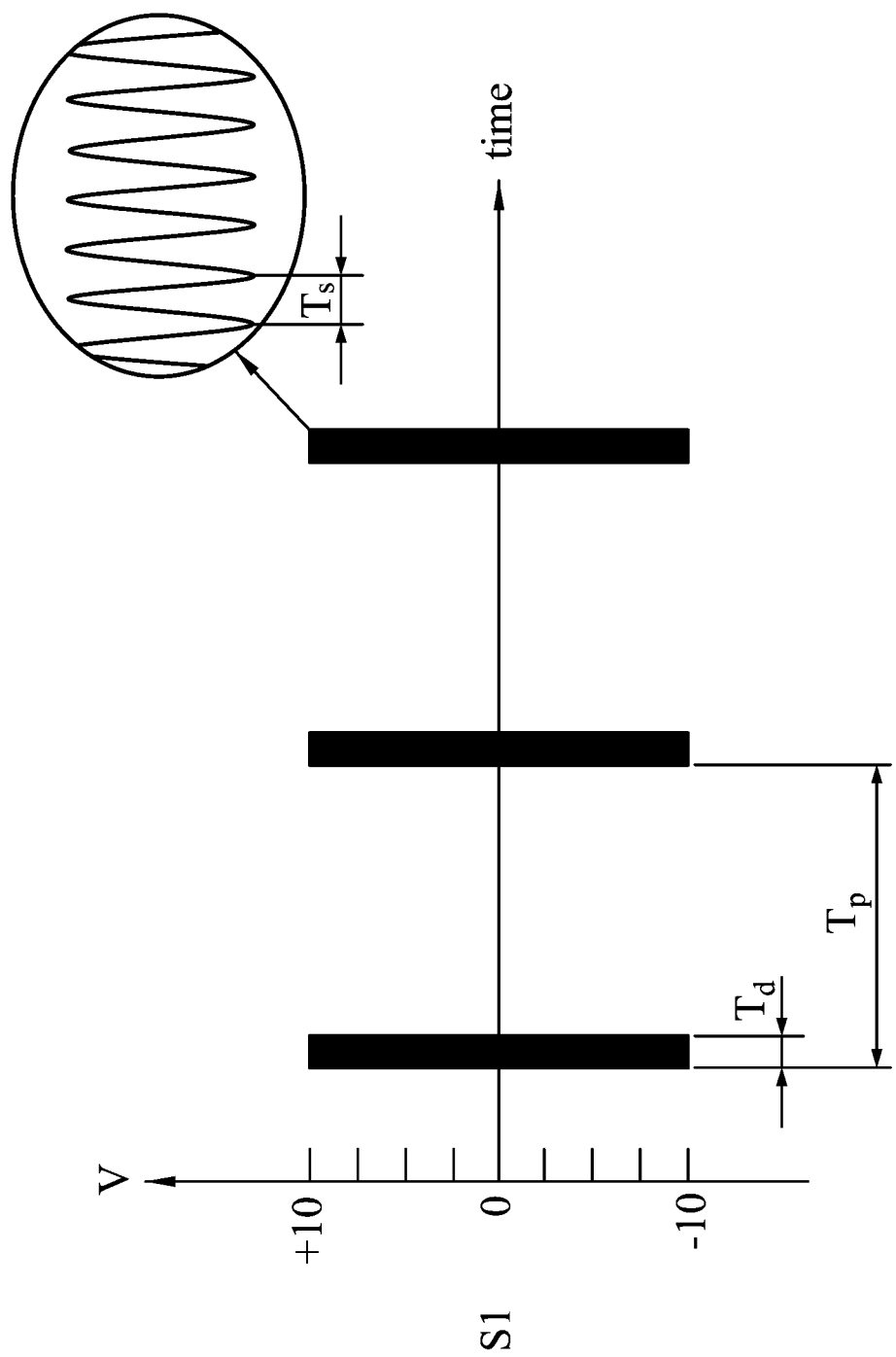
FIG. 2 is a waveform diagram of a first electrical-stimulation signal provided by an electrical-stimulation device according to an embodiment of the disclosure.

FIG. 2 is a waveform diagram of a first electrical-stimulation signal provided by an electrical-stimulation device according to an embodiment of the disclosure. Please refer to FIG. 2. The first electrical-stimulation signal S1 provided by the electrical-stimulation device 120 is, for example, a continuous sinusoidal wave, a continuous triangular wave, or a high-frequency pulsed electrical-stimulation signal, etc., but the embodiment of the disclosure is not limited thereto. In addition, when the first electrical-stimulation signal S1 is a pulse alternating signal, one pulse cycle time Tp includes a plurality of pulse signals and at least one rest period of time, and the pulse cycle time Tp is the reciprocal of the pulse repetition frequency time.

The pulse repetition frequency range (also referred to as the pulse frequency range) is, for example, between 0 (larger than 0) and 1 KHz, preferably between 1 and 100 Hz. In the embodiment, the pulse repetition frequency of the first electrical-stimulation signal S1 is, for example, 2 Hz. In addition, the duration time Td of the plurality of pulses in one pulse cycle time is, for example, between 1 and 250 milliseconds (ms), preferably between 10 and 100 ms. In the embodiment, the duration time Td is, for example, 25 ms. In the embodiment, the frequency of the first electrical-stimulation signal S1 is 600 KHz, in other words, the cycle time Ts of the electrical-stimulation signal is about 1.67 microseconds (μs).

Figure 3:
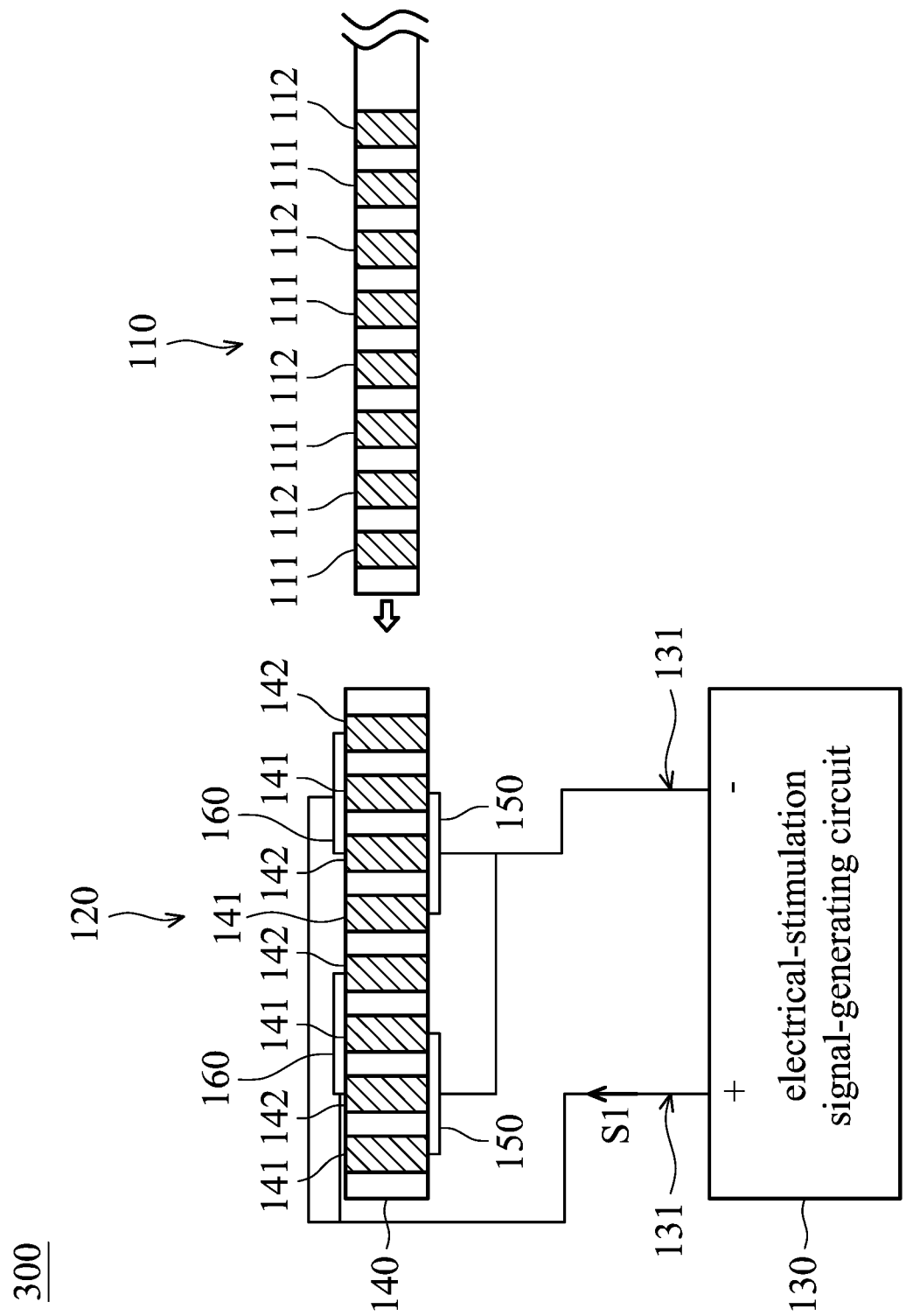
FIG. 3 is a schematic view of an electrical-stimulation system according to another embodiment of the disclosure.

FIG. 3 is a schematic view of an electrical-stimulation system according to another embodiment of the disclosure. The electrical-stimulation system 300 of FIG. 3 is substantially the same as the electrical-stimulation system 100 of FIG. 1. The difference between FIG. 3 and FIG. 1 is that a total number (eight) of first electrodes 111 and the second electrodes 112 of the lead 110 of FIG. 3 is greater than a total number (four) of first electrodes 111 and the second electrodes 112 of the lead 110 of FIG. 1, a total number (eight) of first contact points 141 and the second contact points 142 of the first connection unit 140 of FIG. 3 is greater than a total number (four) of first contact points 141 and the second contact points 142 of the first connection unit 140 of FIG. 1, and a total number (four) of first conductive members 150 and the second conductive members 160 of FIG. 3 is greater than a total number (two) of first conductive member 150 and the second conductive member 160 of FIG. 1.

Similarly, the first conductive members 150 are respectively connected to the first contact points 141, and the second conductive members 160 are respectively connected to the second contact points 142, so as to reduce the required number of external contact points. In addition, the number of first conductive members 150 may increase as the number of first contact points 141 increases, and the number of second conductive members 160 may also increase as the number of second contact points 142 increases. Furthermore, the connection of the first conductive members 150 and the first contact points 141 and the connection of the second conductive members 160 and the second contact points 142 may refer to the embodiment of FIG. 1, and the description thereof is not repeated herein. The two first conductive members 150 and the two second conductive members 160 are respectively connected to the first channel 131, so that the first electrical-stimulation signal S1 is transmitted through the first contact points 141 and the second contact points 142 corresponding to the first channel. Then, the first electrical-stimulation signal S1 is transmitted through the lead 110. Therefore, the number of external contact points of the first contact points 141 and the second contact points 142 with the same electrical polarities may be reduced, and the number of contact points on the connection unit may be adjusted to correspond to the number of first channel 131 provided by the electrical-stimulation signal-generating circuit 130, thereby increasing the flexibility of the connection unit for use.

Figure 4A:
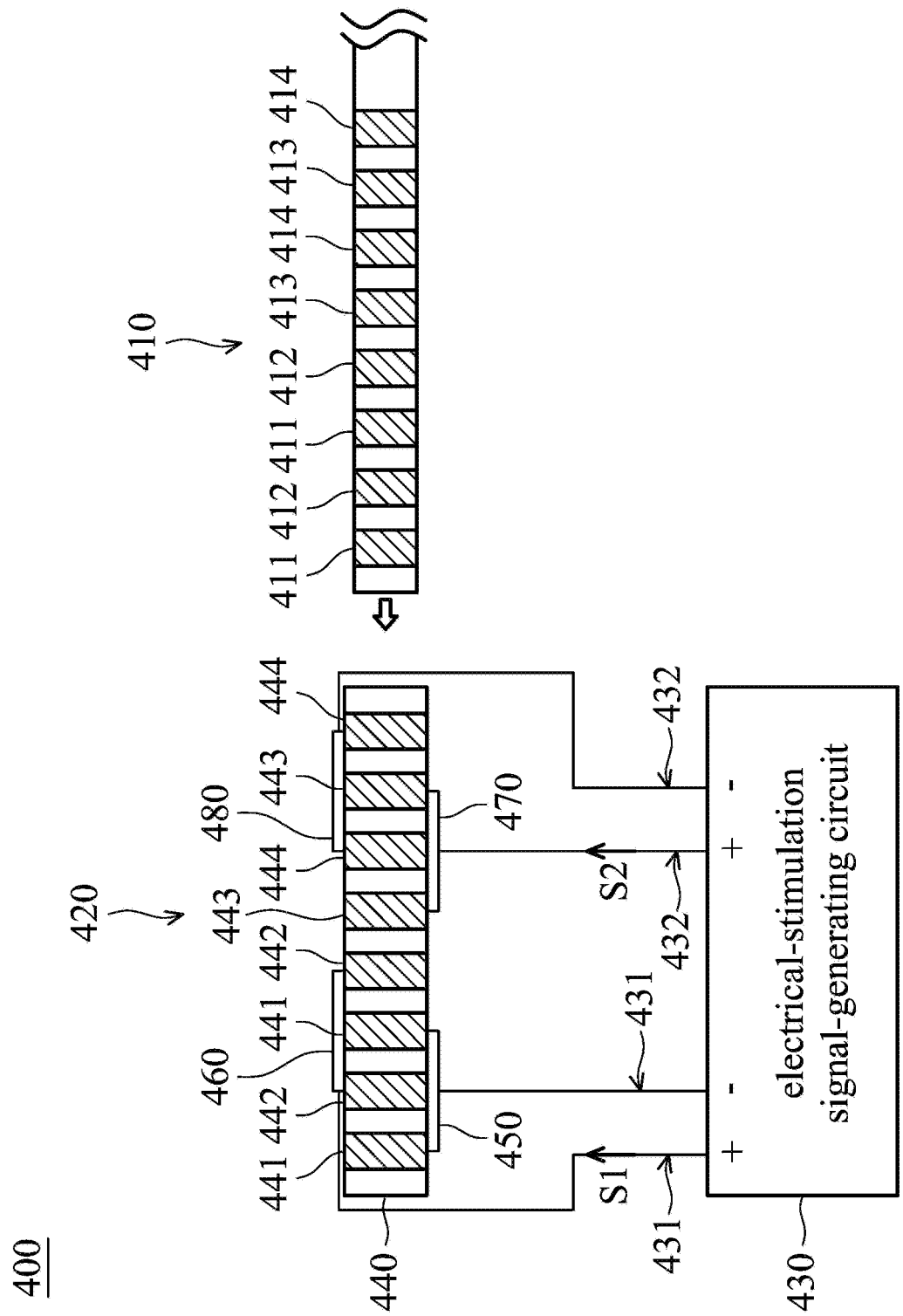
FIGS. 4A and 4B are schematic views of an electrical-stimulation system according to another embodiments of the disclosure.

FIG. 4 is a schematic view of an electrical-stimulation system according to another embodiment of the disclosure. Please refer to FIG. 4. The electrical-stimulation system 400 includes a lead 410 and an electrical-stimulation device 420. The lead 410 includes a plurality of first electrodes 411, a plurality of second electrodes 412, a plurality of third electrodes 413 and a plurality of fourth electrodes 414, wherein the first electrodes 411 and the second electrodes 412 are alternately arranged, and the third electrodes 413 and the fourth electrodes 414 are alternately arranged. In the embodiment, the distance between the first electrode 411 and the second electrode 412 which are adjacent to each other is, for example, between 1 mm and 8 mm, and the distance between the third electrode 413 and the second electrode 414 which are adjacent to each other is between 1 mm and 8 mm.

The electrical-stimulation device 420 is configured to be connected to the lead 410. The electrical-stimulation device 420 includes an electrical-stimulation signal-generating circuit 430, a first connection unit 440, a first conductive member 450, a second conductive member 460, a third conductive member 470 and a fourth conductive member 480. The electrical-stimulation signal-generating circuit 430 has a first channel 431 and a second channel 432 for providing a first electrical-stimulation signal S1 and a second electrical-stimulation signal S2. In the embodiment, the first electrical-stimulation signal S1 and the second electrical-stimulation signal S2 are, for example, a pulse alternating current signal, and the pulse frequency range thereof is, for example, between 0 and 1 KHz. In addition, the intra-pulse frequency ranges of the first electrical-stimulation signal S1 and the second electrical-stimulation signal S2 are, for example, 100 KHz to 1000 KHz and the pulse frequency and the intra-pulse frequency of the second electrical-stimulation signal S2 may be the same or different.

The first connection unit 440 has a plurality of first contact points 441, a plurality of second contact points 442, a plurality of third contact points 443 and a plurality of fourth contact points 444, wherein the first contact points 441 and the second contact points 442 are alternately arranged, and the third contact points 443 and the fourth contact points 444 are alternately arranged. In this embodiment, first connection unit 440 has two first contact points 441, two second contact points 442, two third contact points 443 and two fourth contact points 444. The number of the contact points can be equal or not equal to each other.

In addition, the first contact points 441 of the first connection unit 440 may be correspondingly connected to the first electrodes 411 of the lead 410, respectively. The second contact points 442 of the first connection unit 440 may be correspondingly connected to the second electrodes 412 of the lead 410, respectively. The third contact points 443 of the first connection unit 440 may be correspondingly connected to the third electrodes 413 of the lead 410, respectively. The fourth contact points 444 of the first connection unit 440 may be correspondingly connected to the fourth electrodes 414 of the lead 410, respectively.

Furthermore, a total number of first contact points 441 corresponds to (equals to) a total number of first electrodes 411, a total number of second contact points 442 corresponds to (equals to) a total number of second electrodes 412, a total number of third contact points 443 corresponds to (equals to) a total number of third electrodes 413, and a total number of fourth contact points 444 corresponds to (equals to) a total number of fourth electrodes 414. In the embodiment, electrical polarities of the first contact points 441 and the second contact points 442 and electrical polarities of the third contact points 442 and the fourth contact points 444 may be the same (i.e. when the electrical-stimulation signal is powered by a direct current source), or they may be the opposite (i.e. when the electrical-stimulation signal is an biphasic alternating current (AC) signal). When the electrical polarities of the first contact points 141 and the second contact points 142 and the electrical polarities of the third contact points 442 and the fourth contact points 444 are opposite, the electrical polarities of the first contact points 441 and the third contact points 443 are "positive" and the electrical polarities of the second contact points 442 and the fourth contact points 444 are "negative", or the electrical polarities of the first contact points 441 and the third contact points 443 are "negative" and the electrical polarities of the second contact points 442 and the fourth contact points 444 are "positive". The electrical polarities of first contact points 441 (the same to the first electrodes 411) and the second contact points 442 (the same to the second electrodes 412) will be alternated and the electrical polarities of third contact points 443 (the same to the third electrodes 413) and the fourth contact points 444 (the same to the fourth electrodes 414) will be alternated when the electrical stimulation signals S1, S2 are AC signals.

The first conductive member 450 is connected to at least two first contact points 441. That is, the first conductive member 450 crosses over at least one second contact point 442 to connect together the first contact points 441 that are spaced apart. The second conductive member 460 is connected to at least two second contact points 442. That is, the second conductive member 460 crosses over at least one first contact point 441 to connect together the second contact points 442 that are spaced apart. The third conductive member 470 is connected to at least two third contact points 443. That is, the third conductive member 470 crosses over at least one fourth contact point 444 to connect together the third contact points 443 that are spaced apart. The fourth conductive member 480 is connected to at least two fourth contact points 444. That is, the fourth conductive member 480 crosses over at least one third contact point 443 to connect together the fourth contact points 444 that are spaced apart.

The first conductive member 450 and the second conductive member 460 are electrically connected to the first channel 431, so that the first electrical-stimulation signal S1 is transmitted through the first contact points 441 and the second contact points 442 corresponding to the first channel 431. In addition, the third conductive member 470 and the fourth conductive member 480 are electrically connected to the second channel 432, so that the second electrical-stimulation signal S2 is transmitted through the third contact points 443 and the fourth contact points 444 corresponding to the second channel 432. Then, the first electrical-stimulation signal S1 and the second electrical-stimulation signal S2 are transmitted through the lead 410 in sequence. Therefore, the number of external contact points of the first contact points 441, the second contact points 442, the third contact points 443 and the fourth contact points 444 with the same electrical polarities may be reduced, and the number of contact points on the connection unit may be adjusted to correspond to the number of first channel 431 and second channel 432 provided by the electrical-stimulation signal-generating circuit 430, thereby increasing the flexibility of the connection unit for use.

Figure 5:
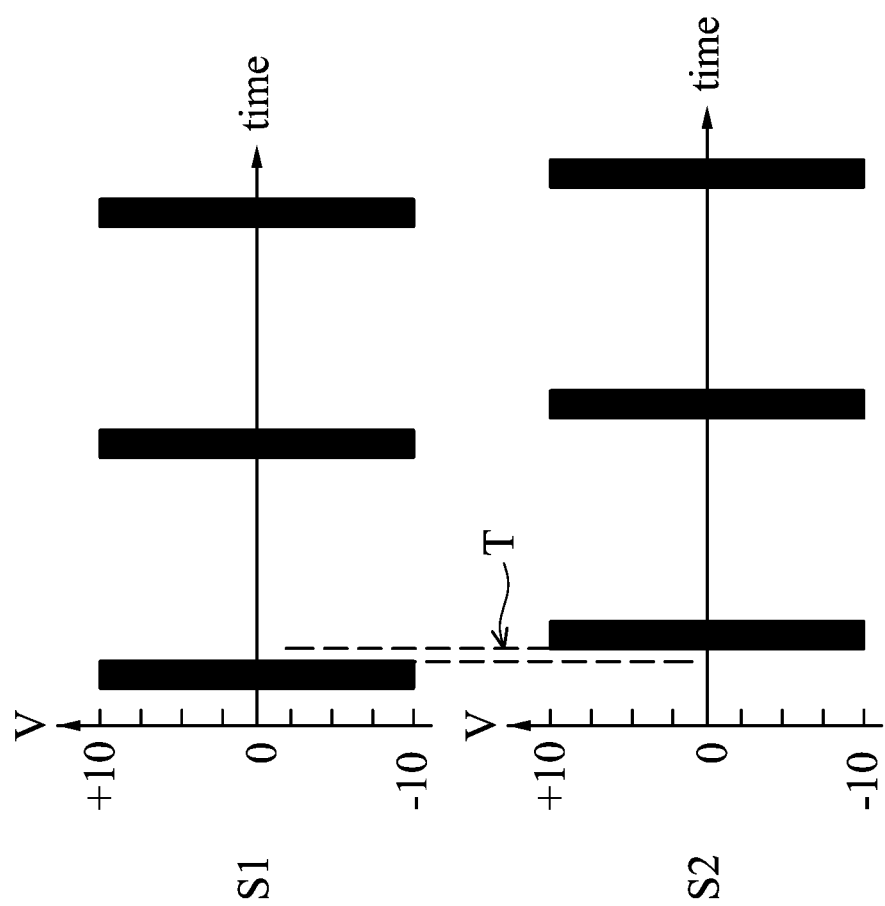
FIG. 5 is a waveform diagram of a first electrical-stimulation signal and a second electrical-stimulation signal provided by an electrical-stimulation device according to an embodiment of the disclosure.

As shown in FIG. 5, in the embodiment, the waveform of the first electrical-stimulation signal S1 provided by the first channel 431 is the same waveform and parameters (such as pulse rate, pulse frequency and signal intensity) of the second electrical-stimulation signal S2 provided by the second channel 432, but a time difference T exits between the pulses. In the embodiment, the time difference T is no larger than the reciprocal of the pulse frequency, for example, between $10^{-3}$ seconds (larger than 0) and 5 seconds, preferred between 0 seconds (larger than 0) and 2 seconds. Therefore, because of the time difference T, for the electrical-stimulation system, the power or energy that the system needs to output per unit time may be small, so that the difficulty of system design may be reduced. The target area of the electrical stimulation may also receive less energy per unit time to ensure the subthreshold stimulation, so that the patient implanted with the electrical-stimulation system may reduce the chance of feeling paresthesia to perform the paresthesia-free treatment. Furthermore, the first electrical-stimulation signal S1 and the second electrical-stimulation signal S2 of FIG. 5 can be the same as or similar to the first electrical-stimulation signal S1 of FIG. 2. The first electrical-stimulation signal S1 and the second electrical-stimulation signal S2 of FIG. 5 may refer to the description of the embodiment of FIG. 2, and the description thereof is not repeated herein.

Figure 4B:
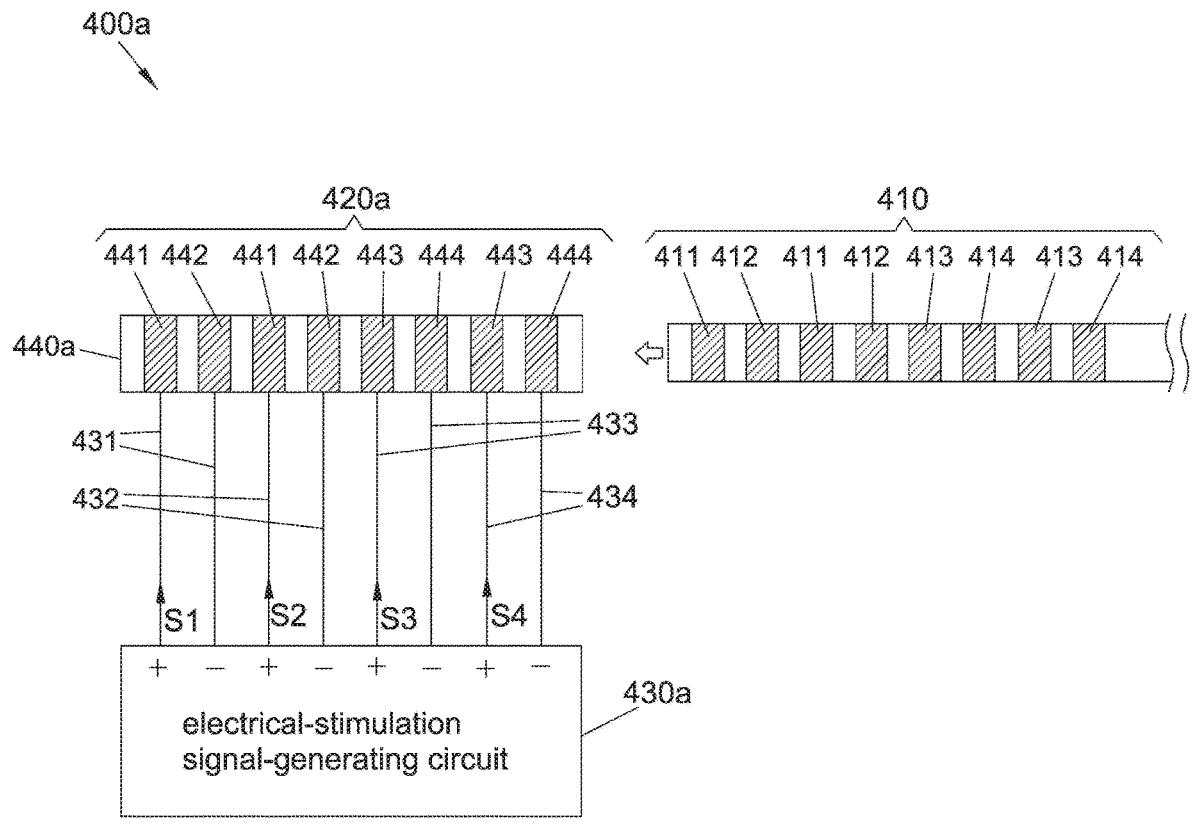

However, the connection unit which transmits the electrical-stimulation signals may not have the conductive members to make different contact points with the same electrical polarity. Referring to FIG. 4B, it shows the electrical-stimulation system 400*a* according to another embodiment of the disclosure. In the electrical-stimulation device 420*a* of the electrical-stimulation system 400*a*, the first connection unit 440*a* has at least one first contact point 441, at least one second contact point 442, at least one third contact point 443 and at least one fourth contact point 444. For example, the first connection unit 440*a* has two first contact point 441, two second contact point 442, two third contact point 443 and two fourth contact points 444. In this embodiment, the first contact point 441 and the second contact point 442 are alternately arranged and the third contact point 443 and the fourth contact point 444 are alternately arranged. Due to not having conductive members, the two first contact point 441 may have same or different electrical polarities, the two second contact point 442 may have same or different electrical polarities, the two third contact point 443 may have same or different electrical polarities and the two fourth contact point 444 may have same or different electrical polarities. The electrical polarities of contact points 441~442 can be listed as: +−+−; +−−+, −+−+; −++− and the electrical polarities of contact points 443~444 can be listed as: +−+−; +−−+, −+−+; −++−. In this case, the first contact points 441 of the first connection unit 440*a* is correspondingly electrically connected to the first electrodes 411 of the lead 410; the second contact points 442 of the first connection unit 440*a* is correspondingly electrically connected to the second electrodes 412 of the lead 410; the third contact points 443 of the first connection unit 440*a* is correspondingly electrically connected to the third electrodes 413 of the lead 410; and the fourth contact points 444 of the first connection unit 440*a* is correspondingly electrically connected to the fourth electrodes 414 of the lead 410. Therefore, the electrical polarities of first contact points 441 and the second contact points 442 are corresponding to (the same as) the electrical polarities of the first electrodes 411 and the second electrodes 412, respectively; and the electrical polarities of third contact points 443 and the fourth contact points 444 are corresponding to (the same as) the electrical polarities of the third electrodes 413 and the fourth electrodes 414, respectively. In this embodiment, the number of the leads can be one lead (with eight electrodes) or two leads (each having four electrodes).

The first channel 431 of the electrical-stimulation signal-generating circuit 430*a* may only control two contact points (one first contact point 441 and one second contact point 442) of the first connection unit 440*a*; the second channel 432 may only control two contact points (one first contact point 441 and one second contact point 442); the third channel 433 may only control two contact points (one third contact point 443 and one fourth contact point 444) and the fourth channel 434 may only control two contact points (one third contact point 443 and one fourth contact point 444). The first channel 431, the second channel 432, the third channel 433 and the fourth channel 434 are sequentially initiated/triggered with a time difference T between the pulse as described above. In the embodiment, the time difference T is no larger than the reciprocal of the pulse frequency, for example, between $10^{-3}$ seconds (larger than 0) and 5 seconds, preferred between 0 seconds (larger than 0) and 2 seconds. Therefore, because of the time difference T, for the electrical-stimulation system, the power or energy that the system needs to output per unit time may become smaller, so that the difficulty of circuit design may be reduced. The target area of the electrical stimulation may also receive less energy per unit time to ensure the subthreshold stimulation, which does not trigger the action potential of neurons. Hence, the patient having the electrical-stimulation system may reduce the chance of feeling paresthesia to perform the paresthesia-free treatment. The illustrative diagram of channels 431~434 transmit electrical-stimulation signals S1~S4 with time difference T is like FIG. 8.

Figure 4C:
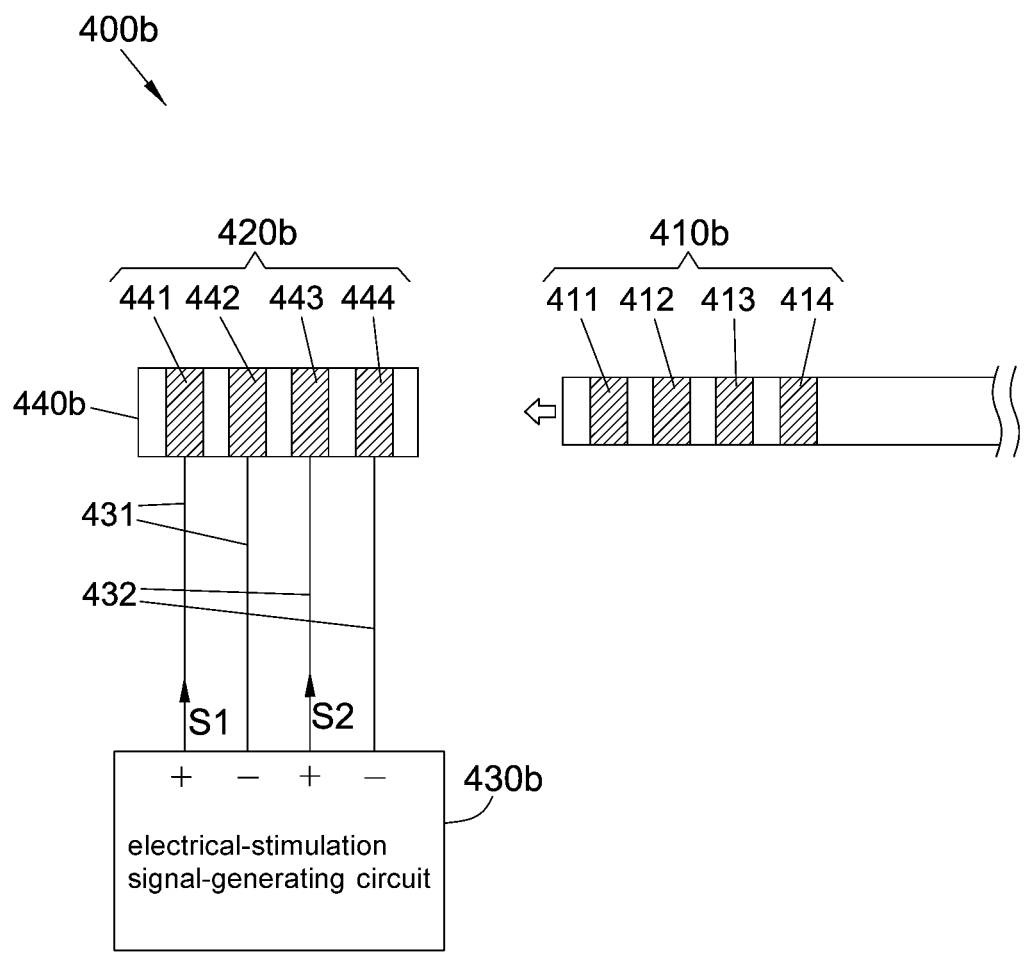
FIG. 4C is a schematic view of an electrical-stimulation system according to another embodiment of the disclosure.

FIG. 4C is a schematic view of an electrical-stimulation system according to another embodiment of the disclosure. The main difference between the electrical-stimulation system 400*b* disclosed in FIG. 4C and the electrical-stimulation system 400*a* disclosed in FIG. 4B is, the first connection unit 440*b* has one first contact point 441, one second contact point 442, one third contact point 443 and one fourth contact point 444. Each of the contact point 441~444 may have same or different electrical polarities. The examples of the electrical polarities of these contact points 441~444 can be listed as: +−+−; +−−+, −+−+; −++−. In this case, the first contact point 441 of the first connection unit 440*b* is correspondingly electrically connected to the first electrode 411 of the lead 410*b*; the second contact point 442 of the first connection unit 440b is correspondingly electrically connected to the second electrode 412 of the lead 410b; the third contact point 443 of the first connection unit 440b is correspondingly electrically connected to the third electrode 413 of the lead 410b; and the fourth contact point 444 of the first connection unit 440b is correspondingly electrically connected to the fourth electrode 414 of the lead 410b.

The first channel 431 of the electrical-stimulation signal-generating circuit 430b only controls two contact points (one first contact point 441 and one second contact point 442) of the first connection unit 440b and the second channel 432 only controls two contact points (one third contact point 443 and one fourth contact point 444). The first channel 431, the second channel 432 are sequentially initiated/triggered with a time difference T between the pulse as described above. In the embodiment, the time difference T is no larger than the reciprocal of the pulse frequency, for example, between $10^{-3}$ seconds (larger than 0) and 5 seconds, preferred between 0 seconds (larger than 0) and 2 seconds. Therefore, because of the time difference T of the electrical-stimulation system 400b, the power or energy that the system needs to output per unit time may become smaller, so that the difficulty of circuit design may be reduced. The target area of the electrical stimulation may also receive less energy per unit time to ensure the subthreshold stimulation, which does not trigger the action potential of neurons. Hence, that the patient having the electrical-stimulation system may reduce the chance of feeling paresthesia to perform the paresthesia-free treatment. The illustrative diagram of channels 431~432 transmit electrical-stimulation signals S1~S2 with time difference T is the same as FIG. 5. Moreover, the number of the connection units in the electrical-stimulation device 420b may be plural, like disclosed in the FIG. 6 and FIG. 7A but without having the conductive members. The numbers of leads in the electrical-stimulation system 400b may be plural corresponding to the numbers of the connection units and the numbers of the electrodes in the lead are corresponding to the numbers of the contact points in the connection units.

Figure 6:
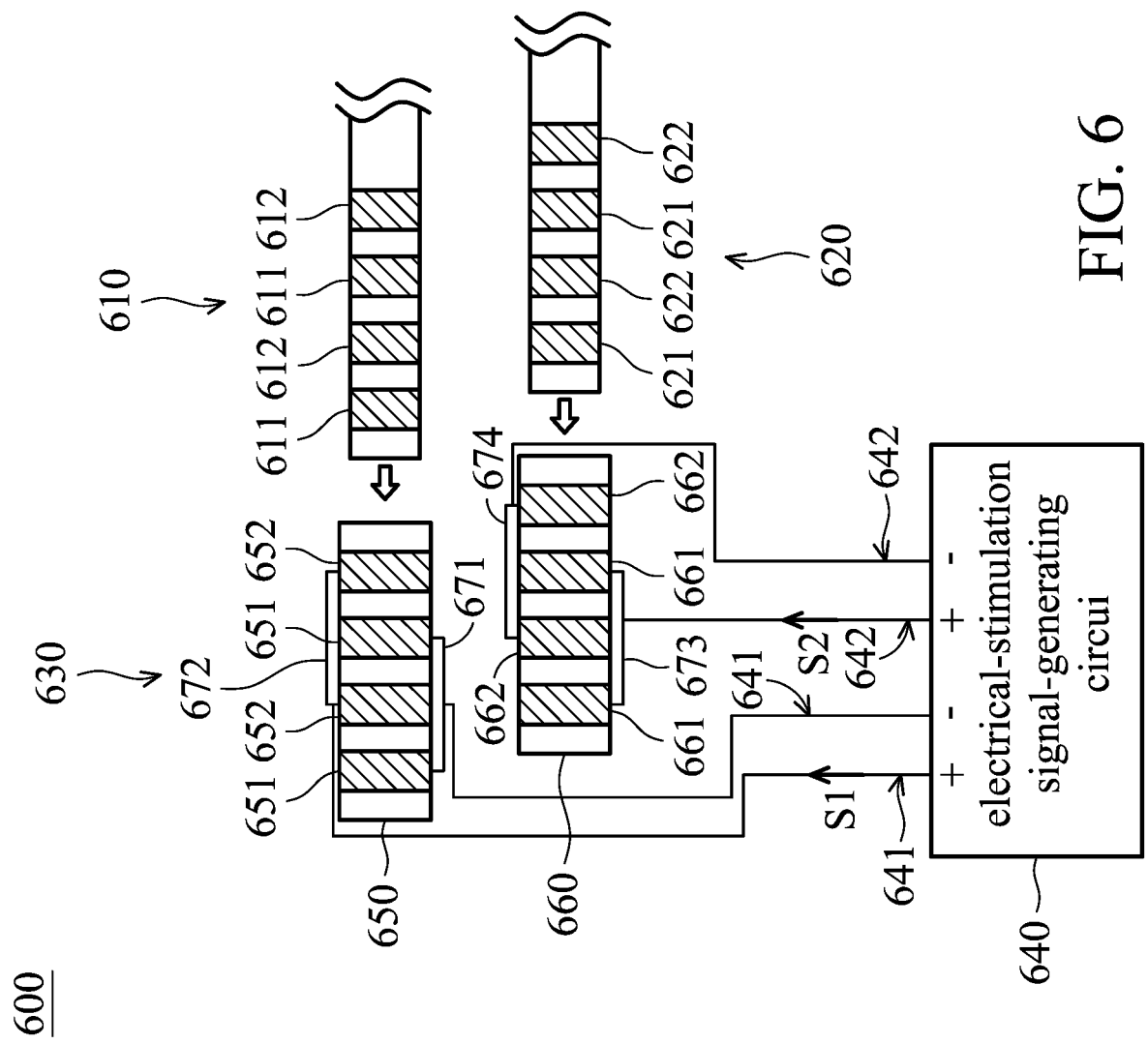
FIG. 6 is a schematic view of an electrical-stimulation system according to another embodiment of the disclosure.

FIG. 6 is a schematic view of an electrical-stimulation system according to another embodiment of the disclosure. Please refer to FIG. 6. The electrical-stimulation system 600 includes a lead 610, a lead 620 and an electrical-stimulation device 630. The lead 610 includes a plurality of first electrodes 611 and a plurality of second electrodes 612, wherein the first electrodes 611 and the second electrodes 612 are alternately arranged (interleaved). The lead 620 includes a plurality of third electrodes 621 and a plurality of fourth electrodes 622, wherein the third electrodes 621 and the fourth electrodes 622 are alternately arranged (interleaved). In the embodiment, the distance between the first electrode 611 and the second electrode 612 which are adjacent to each other is, for example, between 1 mm and 8 mm, and the distance between the third electrode 621 and the fourth electrode 622 which are adjacent to each other is between 1 mm and 8 mm.

The electrical-stimulation device 630 is connected to the lead 610 and the lead 620. The electrical-stimulation device 630 includes an electrical-stimulation signal-generating circuit 640, a first connection unit 650, a second connection unit 660, a first conductive member 671, a second conductive member 672, a third conductive member 673 and a fourth conductive member 674.

The electrical-stimulation signal-generating circuit 640 has a first channel 641 and a second channel 642 for providing a first electrical-stimulation signal S1 and a second electrical-stimulation signal S2. In the embodiment, the first electrical-stimulation signal S1 and the second electrical-stimulation signal S2 are, for example, pulse alternating current signals, and the pulse frequency range thereof is, for example, between 0 and 1 KHz. In addition, the frequency ranges of the first electrical-stimulation signal S1 and the second electrical-stimulation signal S2 are, for example, 100 KHz to 1000 KHz.

The first connection unit 650 has a plurality of first contact points 651 and a plurality of second contact points 652, wherein the first contact points 651 and the second contact points 652 are alternately arranged. The second connection unit 660 has a plurality of third contact points 661 and a plurality of fourth contact points 662, wherein the third contact points 661 and the fourth contact points 662 are alternately arranged.

In addition, the first contact points 651 of the first connection unit 650 may be correspondingly connected to the first electrodes 611 of the lead 610, respectively. The second contact points 652 of the first connection unit 650 may be correspondingly connected to the second electrodes 612 of the lead 610, respectively. The third contact points 661 of the second connection unit 660 may be correspondingly connected to the third electrodes 621 of the lead 620, respectively. The fourth contact points 662 of the second connection unit 660 may be correspondingly connected to the fourth electrodes 622 of the lead 620, respectively.

Furthermore, a total number of first contact points 651 corresponds to a total number of first electrodes 611, a total number of second contact points 652 corresponds to a total number of second electrodes 612, a total number of third contact points 661 corresponds to a total number of third electrodes 621, and a total number of fourth contact points 662 corresponds to a total number of fourth electrodes 622. In the embodiment, electrical polarities of the first contact points 651 and the second contact points 652 and electrical polarities of the third contact points 661 and the fourth contact points 662 may be the same (i.e. when the electrical-stimulation signal is powered by a direct current source), or they may be the opposite (i.e. when the electrical-stimulation signal is an biphasic alternating current (AC) signal). When the electrical polarities of the first contact points 651 and the second contact points 652 and the electrical polarities of the third contact points 661 and the fourth contact points 662 are opposite, the electrical polarities of the first contact points 651 and the third contact points 661 are "positive" and the electrical polarities of the second contact points 652 and the fourth contact points 662 are "negative", or the electrical polarities of the first contact points 651 and the third contact points 661 are "negative" and the electrical polarities of the second contact points 652 and the fourth contact points 662 are "positive". The electrical polarities of the first contact points 651 (the same as the first electrodes 611) and the second contact points 652 (the same as the second electrodes 612) and electrical polarities of the third contact points 661 (the same as the third electrodes 621) and the fourth contact points 662 (the same as the fourth electrodes 622) will be alternated, when the electrical stimulation signals S1, S2 are AC signals.

The first conductive member 671 is connected to at least two first contact points 651. That is, the first conductive member 671 crosses over at least one second contact point 652 to connect together the first contact points 651 that are spaced apart. The second conductive member 672 is connected to at least two second contact points 652. That is, the second conductive member 672 crosses over at least one first contact point 651 to connect together the second contact points 652 that are spaced apart. The third conductive member 673 is connected to at least two third contact points 661. That is, the third conductive member 673 crosses over at least one fourth contact point 662 to connect together the third contact points 661 that are spaced apart. The fourth conductive member 674 is connected to at least two fourth contact points 662. That is, the fourth conductive member 674 crosses over at least one third contact point 661 to connect together the fourth contact points 662 that are spaced apart.

The first conductive member 671 and the second conductive member 672 are electrically connected to the first channel 641, so that the first electrical-stimulation signal S1 is transmitted through the first contact points 651 and the second contact points 652 corresponding to the first channel 641. In addition, the third conductive member 673 and the fourth conductive member 674 are electrically connected to the second channel 642, so that the second electrical-stimulation signal S2 is transmitted through the third contact points 661 and the fourth contact points 662 corresponding to the second channel 642. Then, the first electrical-stimulation signal S1 and the second electrical-stimulation signal S2 are respectively transmitted through the lead 610 and the lead 620 in sequence. Therefore, the number of external contact points of the first contact points 651, the second contact points 652, the third contact points 661 and the fourth contact points 662 with the same electrical polarities may be reduced, and the number of contact points on the connection unit may be adjusted to correspond to the number of first channel 641 and the second channel 642 provided by the electrical-stimulation signal-generating circuit 640, thereby increasing the flexibility of the connection unit for use.

In the embodiment, the waveform of the first electrical-stimulation signal S1 provided by the first channel 641 is the same as the waveform of the second electrical-stimulation signal S2 provided by the second channel 642, but a time difference exits between the pulses, as shown in FIG. 5. In the embodiment, the time difference T is not larger than the reciprocal of the pulse frequency, for example, between 0 seconds and 2 seconds. Due to the time difference between the first channel 641 and the second channel 642, the first channel 641 and the second channel 642 are sequentially initiated/triggered.

Figure 7A:
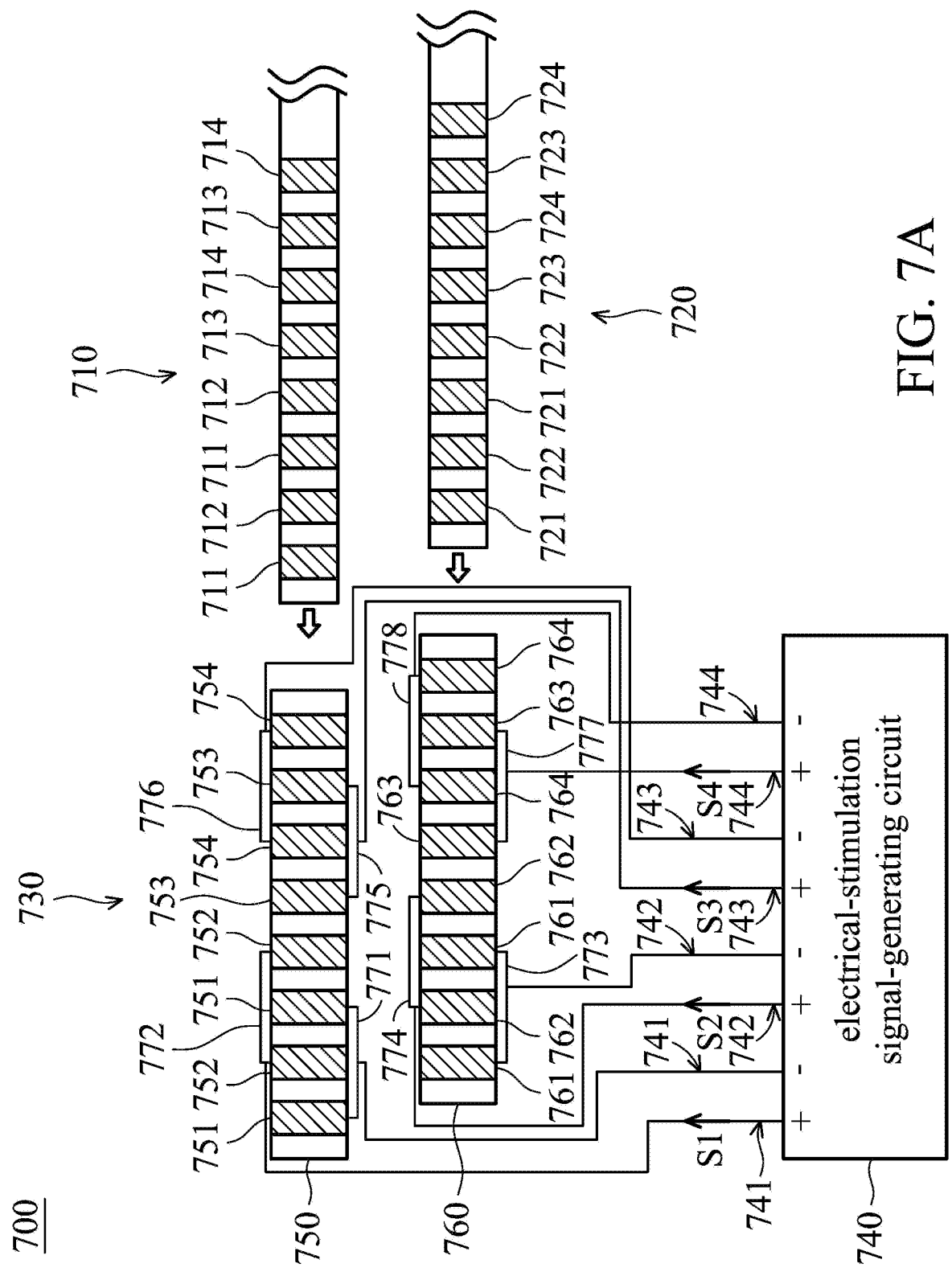
FIGS. 7A and 7B are schematic views of an electrical-stimulation device according to another embodiment of the disclosure.
Figure 7B:
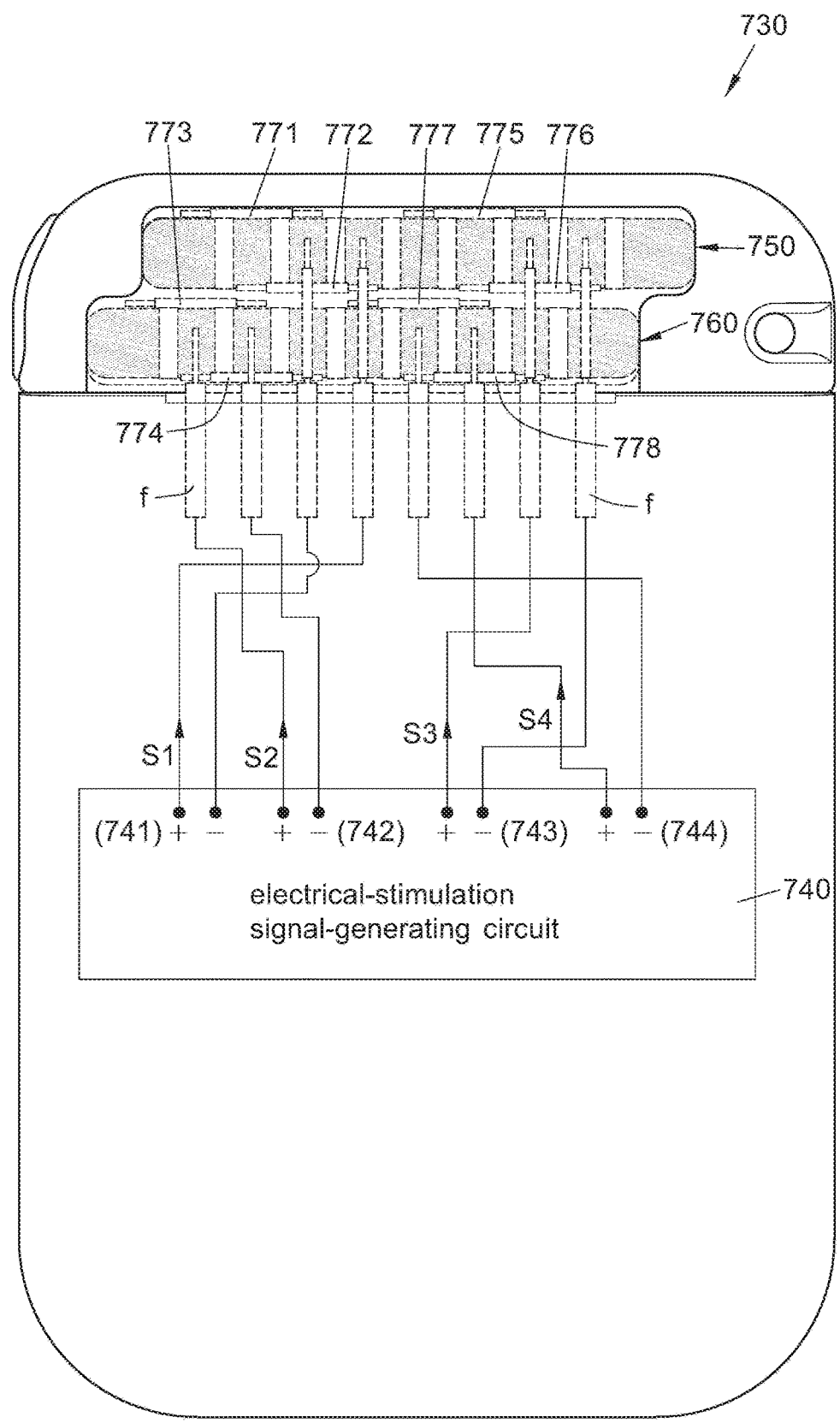

FIGS. 7A and 7B are schematic views of an electrical-stimulation system according to another embodiment of the disclosure. Please refer to FIG. 7A. The electrical-stimulation system 700 includes a lead 710, a lead 720 and an electrical-stimulation device 730. The lead 710 includes a plurality of first electrodes 711, a plurality of second electrodes 712, a plurality of fifth electrodes 713 and a plurality of sixth electrodes 714 wherein the first electrodes 711 and the second electrodes 712 are alternately arranged, and the fifth electrodes 713 and the sixth electrodes 714 are alternately arranged. The lead 720 includes a plurality of third electrodes 721, a plurality of fourth electrodes 722, a plurality of seventh electrodes 723 and a plurality of eighth electrodes 724, wherein the third electrodes 721 and the fourth electrodes 722 are alternately arranged (or interleaved), and the seventh electrodes 723 and the eighth electrodes 724 are alternately arranged (or interleaved).

In the embodiment, the distance between the first electrode 711 and the second electrode 712 which are adjacent to each other is, for example, between 1 mm and 8 mm. The distance between the third electrode 721 the fourth electrode 722 which are adjacent to each other is between 1 mm and 8 mm. The distance between the fifth electrode 713 and the sixth electrode 714 which are adjacent to each other is between 1 mm and 8 mm. The distance between the seventh electrode 723 and the eighth electrodes 724 which are adjacent to each other is between 1 mm and 8 mm.

The electrical-stimulation device 730 is connected to the lead 710 and the lead 720. The electrical-stimulation device 730 includes an electrical-stimulation signal-generating circuit 740, a first connection unit 750, a second connection unit 760, a first conductive member 771, a second conductive member 772, a third conductive member 773, a fourth conductive member 774, a fifth conductive member 775, a sixth conductive member 776, a seventh conductive member 777 and an eighth conductive member 778.

The electrical-stimulation signal-generating circuit 740 has a first channel 741, a second channel 742, a third channel 743 and a fourth channel 744 for providing a first electrical-stimulation signal S1, a second electrical-stimulation signal S2, a third electrical-stimulation signal S3 and a fourth electrical-stimulation signal S4. In the embodiment, the first electrical-stimulation signal S1, the second electrical-stimulation signal S2, the third electrical-stimulation signal S3 and the fourth electrical-stimulation signal S4 are, for example, pulse alternating current signals having biphasic sine or square waveform and the pulse frequency range thereof is, for example, between 0 (larger than 0) and 1 KHz. In addition, the intra-pulse frequency ranges of the first electrical-stimulation signal S1, the second electrical-stimulation signal S2, the third electrical-stimulation signal S3 and the fourth electrical-stimulation signal S4 are, for example, 100 KHz to 1000 KHz.

The first connection unit 750 has a plurality of first contact points 751, a plurality of second contact points 752, a plurality of fifth contact points 753 and a plurality of sixth contact points 754, wherein the first contact points 751 and the second contact points 752 are alternately arranged, and the fifth contact points 753 and the sixth contact points 754 are alternately arranged. The second connection unit 760 has a plurality of third contact points 761, a plurality of fourth contact points 762, a plurality of seventh contact points 763 and a plurality of eighth contact points 764, wherein the third contact points 761 and the fourth contact points 762 are alternately arranged, and the seventh contact points 763 and the eighth contact points 764 are alternately arranged.

In addition, the first contact points 751 of the first connection unit 750 may be correspondingly connected to the first electrodes 711 of the lead 710, respectively. The second contact points 752 of the first connection unit 750 may be correspondingly connected to the second electrodes 712 of the lead 710, respectively. The fifth contact points 753 of the first connection unit 750 may be correspondingly connected to the fifth electrodes 713 of the lead 710, respectively. The sixth contact points 754 of the first connection unit 750 may be correspondingly connected to the sixth electrodes 714 of the lead 710, respectively.

The third contact points 761 of the second connection unit 760 may be correspondingly connected to the third electrodes 721 of the lead 720, respectively. The fourth contact points 762 of the second connection unit 760 may be correspondingly connected to the fourth electrodes 722 of the lead 720, respectively. The seventh contact points 763 of the second connection unit 760 may be correspondingly connected to the seventh electrodes 723 of the lead 720, respectively. The eighth contact points 764 of the second connection unit 760 may be correspondingly connected to the eighth electrodes 724 of the lead 720, respectively.

Furthermore, a total number of first contact points 751 corresponds to a total number of first electrodes 711, a total number of second contact points 752 corresponds to a total number of second electrodes 712, a total number of third contact points 761 corresponds to a total number of third electrodes 721, a total number of fourth contact points 762 corresponds to a total number of fourth electrodes 722, a total number of fifth contact points 753 corresponds to a total number of fifth electrodes 713, a total number of sixth contact points 754 corresponds to a total number of sixth electrodes 714, a total number of seventh contact points 763 corresponds to a total number of seventh electrodes 723, and a total number of eighth contact points 764 corresponds to a total number of eighth electrodes 724.

In the embodiment, electrical polarities of the first contact points 751 and the second contact points 752, electrical polarities of the third contact points 761 and the fourth contact points 762, electrical polarities of the fifth contact points 753 and the sixth contact points 754 and electrical polarities of the seventh contact points 763 and the eighth contact points 764 may be the same, or they may be the opposite. When the electrical polarities of the first contact points 751 and the second contact points 752, the electrical polarities of the third contact points 761 and the fourth contact points 762, the electrical polarities of the fifth contact points 753 and the sixth contact points 754 and the electrical polarities of the seventh contact points 763 and the eighth contact points 764 are opposite, the electrical polarities of the first contact points 751, the third contact points 761, the fifth contact points 753 and the seventh contact points 763 are "positive" and the electrical polarities of the second contact points 752, the fourth contact points 762, the sixth contact points 754 and the eighth contact points 764 are "negative", or the electrical polarities of the first contact points 751, the third contact points 761, the fifth contact points 753 and the seventh contact points 763 are "negative" and the electrical polarities of the second contact points 752, the fourth contact points 762, the sixth contact points 754 and the eighth contact points 764 are "positive". The electrical polarities of first contact points 751 (the same to the first electrodes 711) and the second contact points 752 (the same to the second electrodes 712) will be alternated and the electrical polarities of third contact points 753 (the same to the third electrodes 713) and the fourth contact points 754 (the same to the fourth electrodes 714) will be alternated when the electrical stimulation signals S1, S2 are AC signals.

The first conductive member 771 is connected to at least two first contact points 751. That is, the first conductive member 771 crosses over at least one second contact point 752 to connect together the first contact points 751 that are spaced apart. The second conductive member 772 is connected to at least two second contact points 752. That is, the second conductive member 772 crosses over at least one first contact point 751 to connect together the second contact points 752 that are spaced apart. The third conductive member 773 is connected to at least two third contact points 761. That is, the third conductive member 773 crosses over at least one fourth contact point 762 to connect together the third contact points 761 that are spaced apart. The fourth conductive member 774 is connected to at least two fourth contact points 762. That is, the fourth conductive member 774 crosses over at least one third contact point 761 to connect together the fourth contact points 762 that are spaced apart.

The fifth conductive member 775 is connected to at least two fifth contact points 753. That is, the fifth conductive member 775 crosses over at least one sixth contact point 754 to connect together the fifth contact points 753 that are spaced apart. The sixth conductive member 776 is connected to at least two sixth contact points 754. That is, the sixth conductive member 776 crosses over at least one fifth contact point 753 to connect together the sixth contact points 754 that are spaced apart. The seventh conductive member 777 is connected to at least two seventh contact points 763. That is, the seventh conductive member 777 crosses over at least one eighth contact point 764 to connect together the seventh contact points 763 that are spaced apart. The eighth conductive member 778 is connected to at least two eighth contact points 764. That is, the eighth conductive member 778 crosses over at least one seventh contact point 763 to connect together the eighth contact points 764 that are spaced apart.

Referring to FIG. 7A and FIG. 7B, the electrical-stimulation signals S1~S4 generated from the electrical stimulation signal generating circuit 740 are transmitted by the first channel 741, the second channel 742, the third channel 743 and the fourth channel 744. Then, the electrical-stimulation signal S1, S2 are conducted by different feedthroughs (f) of the electrical stimulation signal generating circuit 740, and corresponding conductive elements to the corresponding conductive members (771~778) and are transmitted to the corresponding contact points (751~754; 761~764). Afterward, the first electrical-stimulation signal S1 will be transmitted through the electrical polarity alternated first electrodes 711 and the second electrodes 712 of the lead 710; the second electrical-stimulation signal S2 will be transmitted through the electrical polarity alternated third electrodes 721 and the fourth electrodes 722 of the lead 720; the third electrical-stimulation signal S3 will be transmitted through the electrical polarity alternated fifth electrodes 713 and the sixth electrodes 714 of the lead 710 and the fourth electrical-stimulation signal S4 will be transmitted through the electrical polarity alternated seventh electrodes 723 and the eighth electrodes 724. Two of the first contact points 751 are connected through the first conductive members 771, two of the second contact points 752 are connected through the second conductive members 772, which resulted in the same electrical polarity of the two first electrodes 711 and the same electrical polarity of the two second electrodes 712, respectively. Likewise, the same electrical polarity of the two of third electrodes 721, the same electrical polarity of the two of fourth electrodes 722, the same electrical polarity of the two of fifth electrodes 713, the same electrical polarity of the two sixth electrodes 714, the same electrical polarity of the two of seventh electrodes 723, and the same electrical polarity of the two of eighth electrodes 724, respectively. The first conductive member 771 and the second conductive member 772 are electrically connected to the first channel 741, so that the first electrical-stimulation signal S1 is transmitted through the first contact points 751 and the second contact points 752 corresponding to the first channel 741. In addition, the third conductive member 773 and the fourth conductive member 774 are electrically connected to the second channel 742, so that the second electrical-stimulation signal S2 is transmitted through the third contact points 761 and the fourth contact points 762 corresponding to the second channel 742. The fifth conductive member 775 and the sixth conductive member 776 are electrically connected to the third channel 743, so that the third electrical-stimulation signal S3 is transmitted through the fifth contact points 753 and the sixth contact points 754 corresponding to the third channel 743. The seventh conductive member 777 and the eighth conductive member 778 are electrically connected to the fourth channel 744 so that the fourth electrical-stimulation signal S4 is transmitted through the seventh contact points 763 and the eighth contact points 764 corresponding to the fourth channel 744. Then, the first electrical-stimulation signal S1, the second electrical-stimulation signal S2, the third electrical-stimulation signal S3 and the fourth electrical-stimulation signal S4 are respectively transmitted through the lead 710 and the lead 720.

Thus, eight electrodes 711~714 of the lead 710 only need two output channel 741, 743 of the electrical-stimulation signal-generating circuit 740 to electrically connect to the first, second, fifth, sixth conductive members 771, 772, 775, 776; and eight electrodes 721~724 of the lead 720 only need two output channel 742, 744 of the electrical-stimulation signal-generating circuit 740 to electrically connect to the third, fourth, seventh, eighth conductive members 773, 774, 777, 778. There is no need to use eight channels to the control the parameters (such as pulse rate, pulse frequency and signal intensity) of the electrical-stimulation signals S1~S4, which can reduce the needed number of feedthroughs f for connection between the channels 741~744 and the contact points 751~754, 761~764 and reduce the needed number of channels. Therefore, the eight contact points of the connection unit of one lead may be adjusted to two electrical polarities, which means at least the lead only needs one channel to control them. In this embodiment, the lead 710 is controlled by two channels 741, 743 and the lead 720 is controlled by another two channels 742, 744, thereby increasing the flexibility of the connection unit for use. Moreover, the size of the electrical-stimulation device can be reduced owing to the reduced number of channels of the electrical-stimulation signal-generating circuit or the reduced number of feedthroughs for connection between the channel and the contact points. On the other side, it's much easier for clinician/user to use or setup the device/system. When the system is on, the polarities of the contact points are determined, thus the polarities of electrodes of the lead are determined to be interleaved, which can reduce the device/system setup time.

Figure 8:
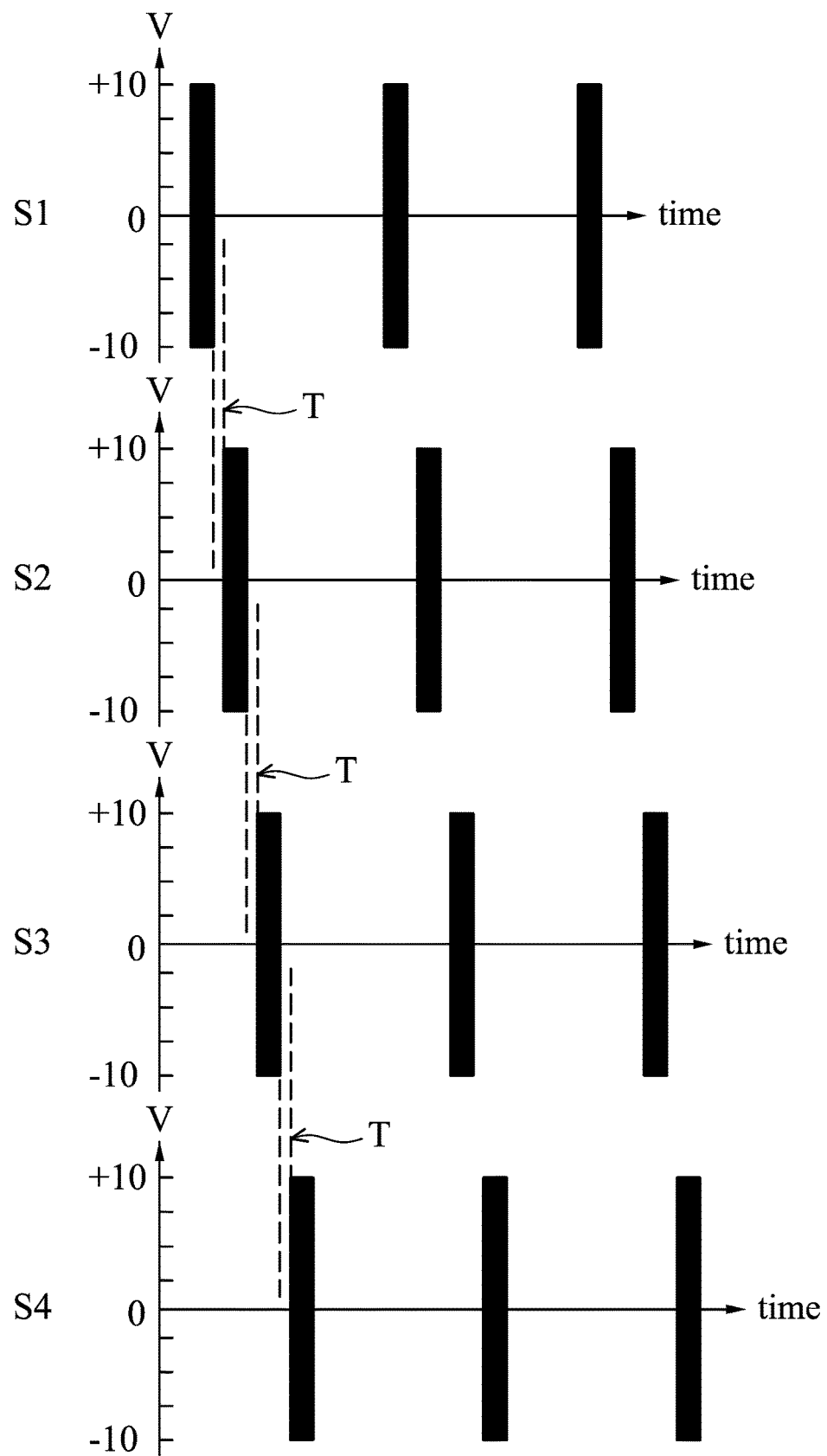
FIG. 8 is a waveform diagram of a first electrical-stimulation signal, a second electrical-stimulation signal, a third electrical-stimulation signal and a fourth electrical-stimulation signal provided by an electrical-stimulation device according to an embodiment of the disclosure.

As shown in FIG. 8, in the embodiment, the waveform of the first electrical-stimulation signal S1 provided by the first channel 741 is substantially the same as the waveform of the second electrical-stimulation signal S2 provided by the second channel 742, but a time difference T between the pulses. The waveform of the second electrical-stimulation signal S2 provided by the second channel 742 is substantially the same as the waveform of the third electrical-stimulation signal S3 provided by the third channel 743, but a time difference T exists between the pulses. The waveform of the third electrical-stimulation signal S3 provided by the third channel 743 is substantially the same as the waveform of the fourth electrical-stimulation signal S4 provided by the fourth channel 744, but a time difference T exists between the pulses. In the embodiment, the time difference T is not larger than the reciprocal of the pulse frequency, for example, between 0 seconds and 2 seconds. Due to the time difference between the first channel 741, the second channel 742, third channel 743 and the fourth channel 744, the first channel 741, the second channel 742, third channel 743 and the fourth channel 744 are sequentially initiated/triggered.

In addition, the first electrical-stimulation signal S1, the second electrical-stimulation signal S2, the third electrical-stimulation signal S3 and the fourth electrical-stimulation signal S4 of FIG. 8 are the same as or similar to the first electrical-stimulation signal S1 of FIG. 2. The first electrical-stimulation signal S1, the second electrical-stimulation signal S2, the third electrical-stimulation signal S3 and the fourth electrical-stimulation signal S4 of FIG. 8 may refer to the description of the embodiment of FIG. 2, and the description thereof is not repeated herein.

Figure 9:
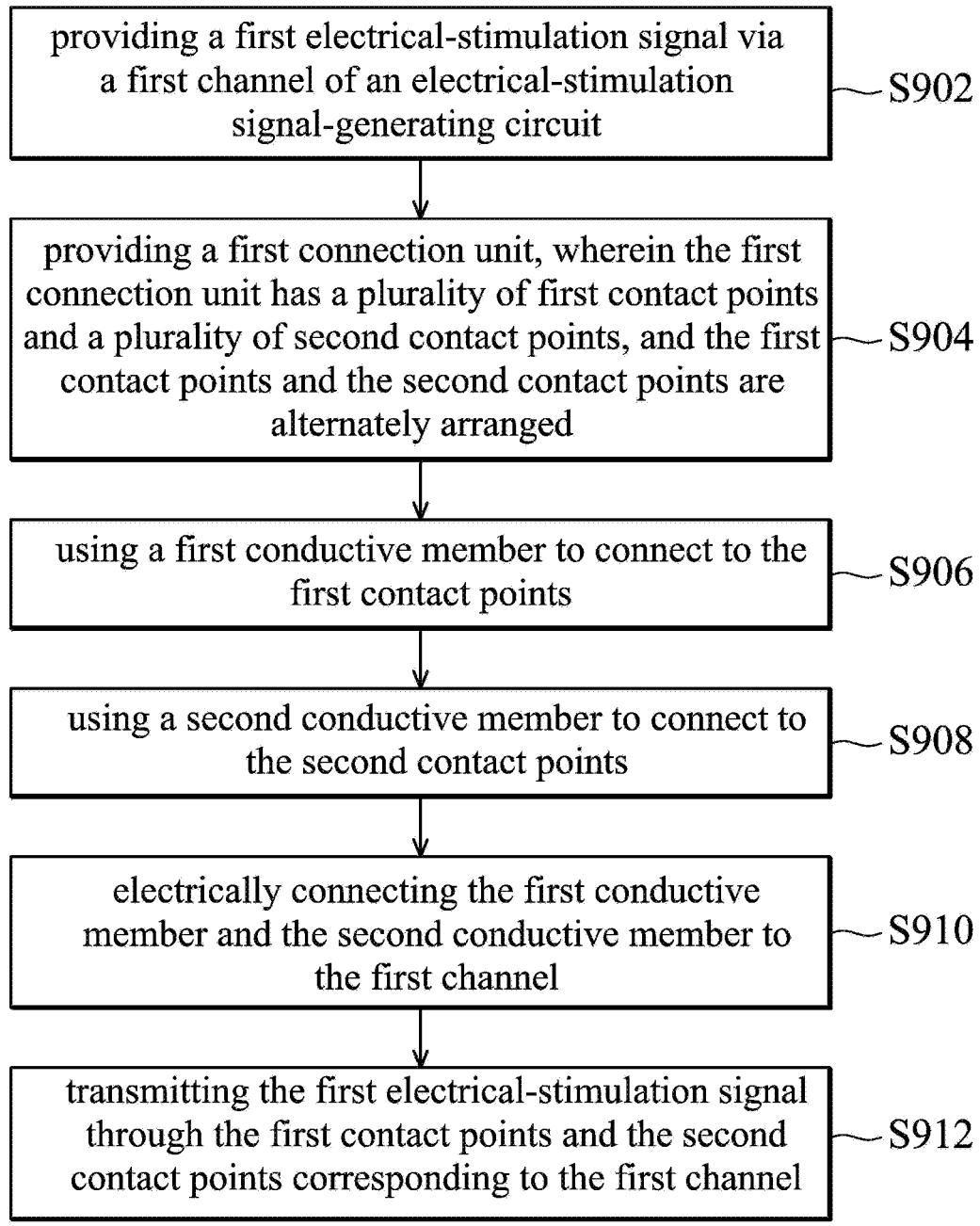
FIG. 9 is a flowchart of an operation method of an electrical-stimulation device according to an embodiment of the disclosure.

According to the above-mentioned description, the above embodiments may introduce an operation method of an electrical-stimulation device. FIG. 9 is a flowchart of an operation method of an electrical-stimulation device according to an embodiment of the disclosure. In step S902, the method involves providing a first electrical-stimulation signal via a first channel of an electrical-stimulation signal-generating circuit. In step S904, the method involves providing a first connection unit, wherein the first connection unit has a plurality of first contact points and a plurality of second contact points, and the first contact points and the second contact points are alternately arranged.

In step S906, the method involves using a first conductive member to connect to the first contact points. In step S908, the method involves using a second conductive member to connect to the second contact points. In step S910, the method involves electrically connecting the first conductive member and the second conductive member to the first channel. In step S912, the method involves transmitting the first electrical-stimulation signal through the first contact points and the second contact points corresponding to the first channel.

Figure 10:
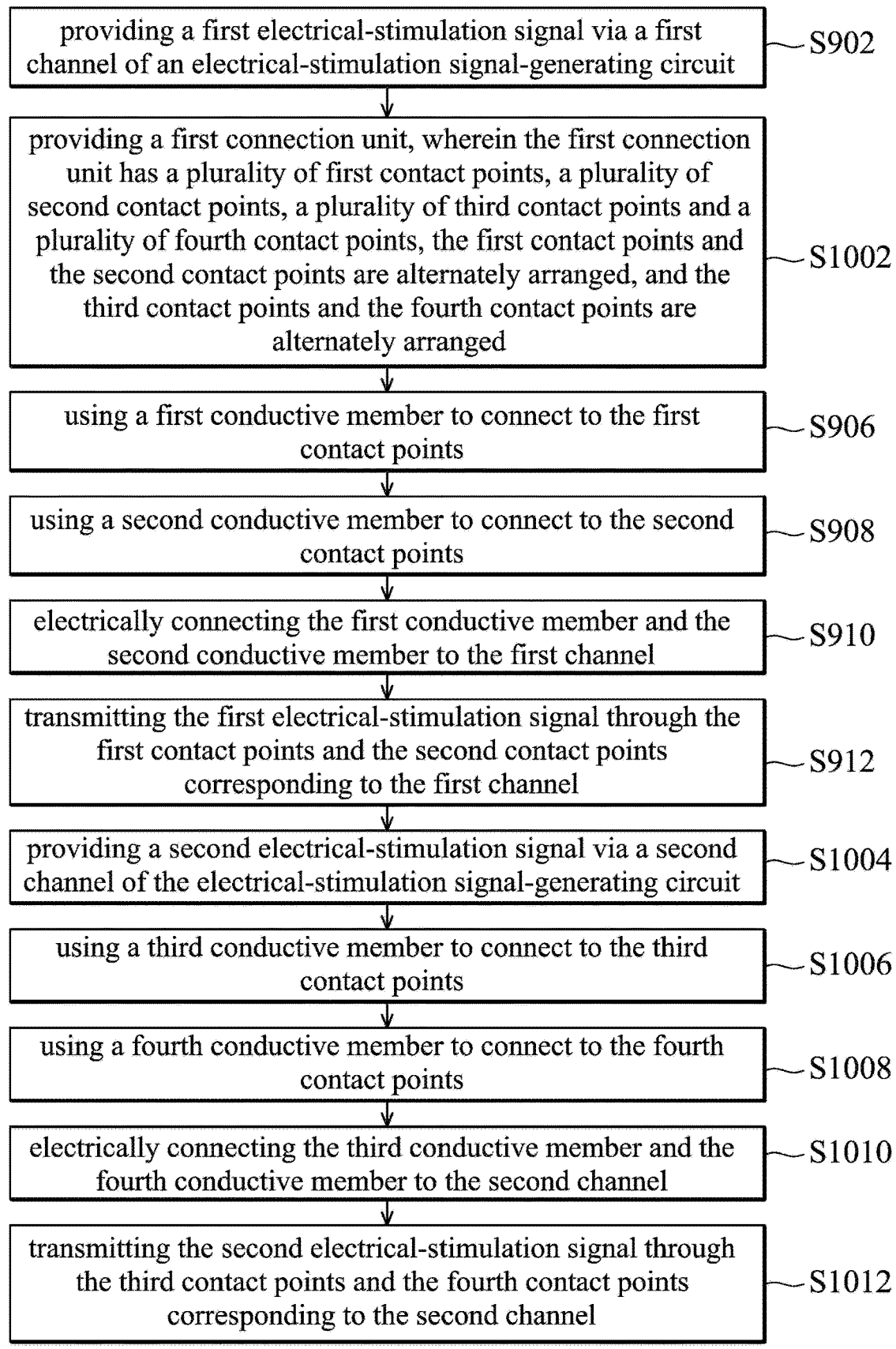
FIG. 10 is a flowchart of an operation method of an electrical-stimulation device according to another embodiment of the disclosure.

FIG. 10 is a flowchart of an operation method of an electrical-stimulation device according to another embodiment of the disclosure. In the embodiment, steps S902 and S906~S912 in FIG. 10 are identical to or similar to steps S902 and S906~S912 in FIG. 9. Accordingly, steps S902 and S906~S912 in FIG. 10 may refer to the description of the embodiment of FIG. 9, and the description thereof is not repeated herein.

In step S1002, the method involves providing a first connection unit, wherein the first connection unit has a plurality of first contact points, a plurality of second contact points, a plurality of third contact points and a plurality of fourth contact points, the first contact points and the second contact points are alternately arranged, and the third contact points and the fourth contact points are alternately arranged.

In step S1004, the method involves providing a second electrical-stimulation signal via a second channel of the electrical-stimulation signal-generating circuit. In step S1006, the method involves using a third conductive member to connect to the third contact points. In step S1008, the method involves using a fourth conductive member to connect to the fourth contact points. In step S1010, the method involves electrically connecting the third conductive member and the fourth conductive member to the second channel. In step S1012, the method involves transmitting the second electrical-stimulation signal through the third contact points and the fourth contact points corresponding to the second channel. In the embodiment, a time difference exists between the first electrical-stimulation signal provided by the first channel and the second electrical-stimulation signal provided by the second channel. In addition, the time difference is between 0 seconds and 2 seconds.

Figure 11A:
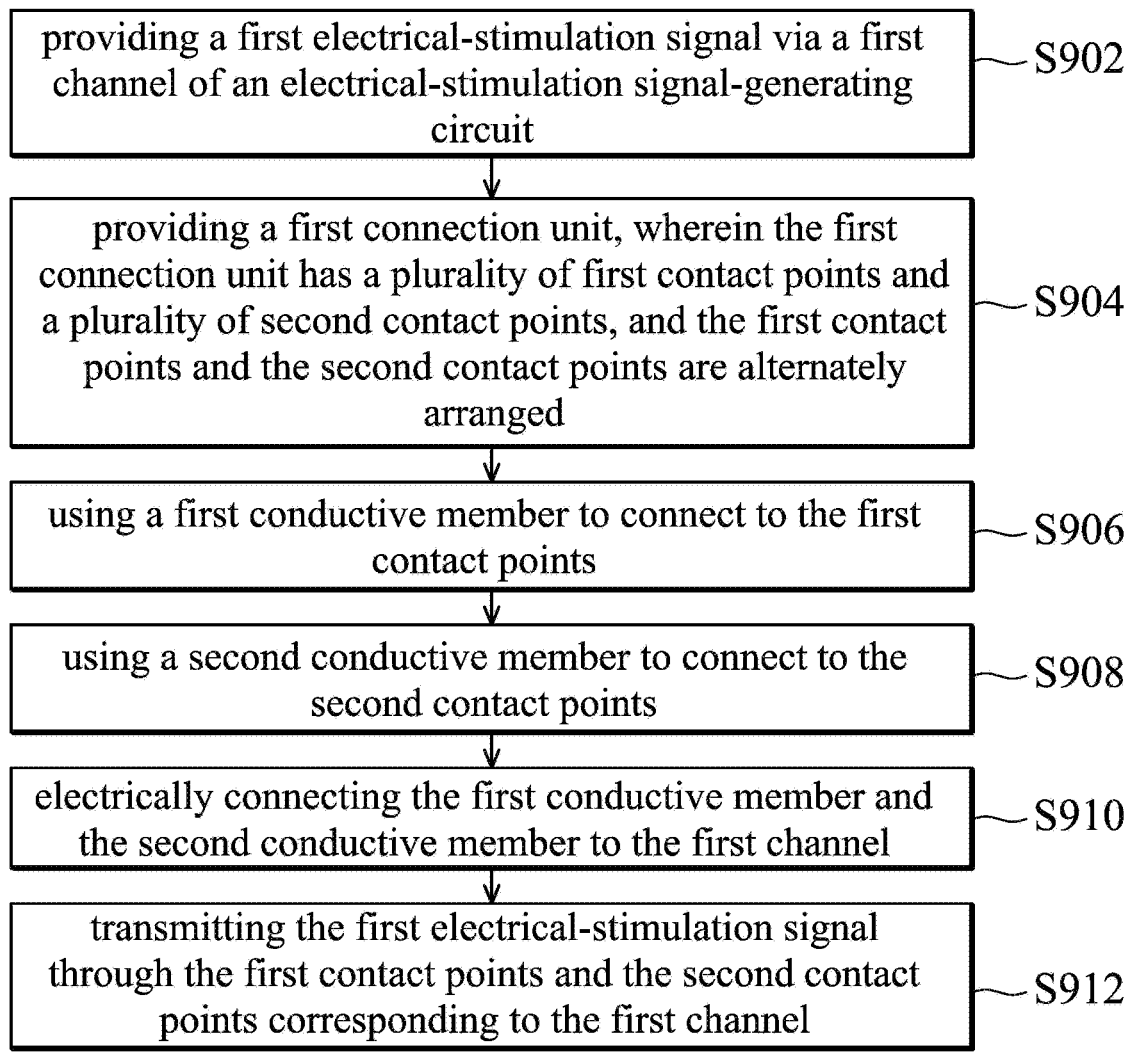
FIGS. 11A and 11B are a flowchart of an operation method of an electrical-stimulation device according to another embodiment of the disclosure.
Figure 11B:
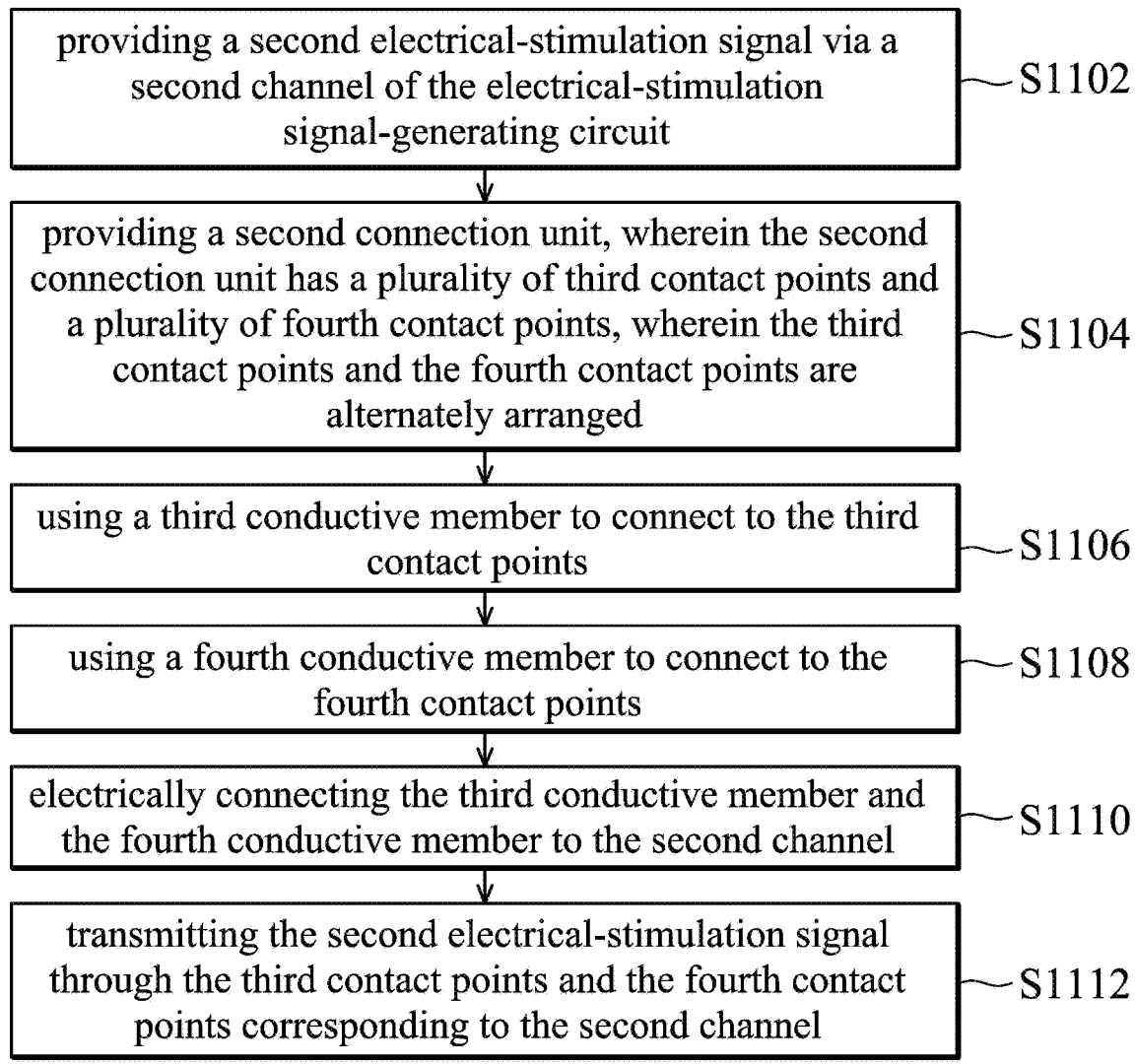

FIGS. 11A and 11B are a flowchart of an operation method of an electrical-stimulation device according to another embodiment of the disclosure. In the embodiment, steps S902~S912 in FIG. 11A are identical to or similar to steps S902~S912 in FIG. 9. Accordingly, S902~S912 in FIG. 11A may refer to the description of the embodiment of FIG. 9, and the description thereof is not repeated herein.

In step S1102, the method involves providing a second electrical-stimulation signal via a second channel of the electrical-stimulation signal-generating circuit. In step S1104, the method involves providing a second connection unit, wherein the second connection unit has a plurality of third contact points and a plurality of fourth contact points, wherein the third contact points and the fourth contact points are alternately arranged.

In step S1106, the method involves using a third conductive member to connect to the third contact points. In step S1108, the method involves using a fourth conductive member to connect to the fourth contact points. In step S1110, the method involves electrically connecting the third conductive member and the fourth conductive member to the second channel. In step S1112, the method involves transmitting the second electrical-stimulation signal through the third contact points and the fourth contact points corresponding to the second channel. In the embodiment, the first electrical-stimulation signal is an alternating current signal, and the pulse frequency range thereof is between 0 (larger than 0) and 1 KHz. In addition, the intra-pulse frequency range of the first electrical-stimulation signal is 100 KHz to 1000 KHz.

FIG. 12 is a flowchart of an operation method of an electrical-stimulation system according to an embodiment of the disclosure. In the embodiment, the operation method of an electrical-stimulation system may include step S902~S912 in FIG. 9 (not shown) and step S1202. In step S1202, the method involves providing a lead for electrically connecting the first connection unit.

FIG. 13 is a flowchart of an operation method of an electrical-stimulation system according to another embodiment of the disclosure. In the embodiment, the operation method of an electrical-stimulation system may include steps S902, S906~S912, and S1002~S1012 in FIG. 10 (not shown) and steps S1302. In step S1302, the method involves providing a lead for electrically connecting the first connection unit.

FIG. 14 is a flowchart of an operation method of an electrical-stimulation system according to another embodiment of the disclosure. In the embodiment, the operation method of an electrical-stimulation system may include step S902~S912 in FIG. 11A (not shown), step S1102~S1112 in FIG. 11B (not shown) and steps S1402 and S1404. In step S1402, the method involves providing a first lead for electrically connecting the first connection unit. In step S1404, the method involves providing a second lead for electrically connecting the second connection unit.

It should be noted that the order of the steps of FIG. 9, FIG. 10, FIG. 11A, FIG. 11B, FIG. 12, FIG. 13 and FIG. 14 is only for illustrative purpose, but not intended to limit the order of the steps of the present disclosure. The user may change the order of the steps above according the requirements thereof. The flowcharts described above may add additional steps or use fewer steps without departing from the spirit and scope of the present disclosure.

In summary, according to the electrical-stimulation device and the operation method thereof and the electrical-stimulation system disclosed by the disclosure, at least two of the contact points of the connection unit are connected through the conductive member resulted in the same electrical polarity to reduce the corresponding needed number of channels of the electrical-stimulation signal-generating circuit for providing the electrical-stimulation signal and reduce the needed number of feedthroughs for connection between the channel and the contact points. The electrical-stimulation signal provided by the channel of the electrical-stimulation signal-generating circuit may be transmitted through the corresponding contact points. Moreover, the size of the electrical-stimulation device can be reduced owing to the reduced number of channel of the electrical-stimulation signal-generating circuit or the reduced number of feedthroughs for connection between the channel and the contact points. In addition, when there are multiple channels of the electrical-stimulation signal-generating circuit, the electrical-stimulation signals generated by these channels may be sequentially transmitted at an interval of the time difference to achieve the corresponding effect. Therefore, even if the number of contact points of the connection unit and the number of channel are different, the connection unit and the channel may still corresponded to each other by the conductive member, thereby effectively increasing the flexibility of the connection unit for use. On the other side, it's much easier for clinician to use or setup the device/system. When the system is on, the polarities of the contact points are determined, thus the polarities of electrodes of the lead are determined to be interleaved, which can reduce the device/system setup time.

While the disclosure has been described by way of example and in terms of the preferred embodiments, it should be understood that the disclosure is not limited to the disclosed embodiments. On the contrary, it is intended to cover various modifications and similar arrangements (as would be apparent to those skilled in the art). Therefore, the scope of the appended claims should be accorded the broadest interpretation to encompass all such modifications and similar arrangements.

What is claimed is:

1. An electrical-stimulation device, comprising:
an electrical-stimulation signal-generating circuit, having a first channel for providing a first electrical-stimulation signal;
a first connection unit, having a plurality of first contact points and a plurality of second contact points, wherein the first contact points and the second contact points are alternately arranged;
a first conductive member, connected to the first contact points; and
a second conductive member, connected to the second contact points;
wherein the first conductive member and the second conductive member are electrically connected to the first channel, so that the first electrical-stimulation signal is transmitted through the first contact points and the second contact points corresponding to the first channel.

2. The electrical-stimulation device as claimed in claim 1, wherein the first connection unit further has a plurality of third contact points and a plurality of fourth contact points, the third contact points and the fourth contact points are alternately arranged, the electrical-stimulation signal-generating circuit further comprises a second channel for providing a second electrical-stimulation signal, and the electrical-stimulation device further comprises:
a third conductive member, connected to the third contact points; and
a fourth conductive member, connected to the fourth contact points;
wherein the third conductive member and the fourth conductive member are electrically connected to the second channel, so that the second electrical-stimulation signal is transmitted through the third contact points and the fourth contact points corresponding to the second channel.

3. The electrical-stimulation device as claimed in claim 2, wherein a time difference exists between the first electrical-stimulation signal provided by the first channel and the second electrical-stimulation signal provided by the second channel.

4. The electrical-stimulation device as claimed in claim 3, wherein the time difference is between 0 seconds and 2 seconds.

5. The electrical-stimulation device as claimed in claim 1, wherein the electrical-stimulation signal-generating circuit further comprises a second channel for providing a second electrical-stimulation signal, and the electrical-stimulation device further comprises:
 a second connection unit, having a plurality of third contact points and a plurality of fourth contact points, wherein the third contact points and the fourth contact points are alternately arranged;
 a third conductive member, connected to the third contact points; and
 a fourth conductive member, connected to the fourth contact points;
 wherein the third conductive member and the fourth conductive member are electrically connected to the second channel, so that the second electrical-stimulation signal is transmitted through the third contact points and the fourth contact points corresponding to the second channel.

6. The electrical-stimulation device as claimed in claim 5, wherein the first connection unit further has a plurality of fifth contact points and a plurality of sixth contact points, the fifth contact points and the sixth contact points are alternately arranged, the second connection unit further has a plurality of seventh contact points and a plurality of eighth contact points, the seventh contact points and the eighth contact points are alternately arranged, the electrical-stimulation signal-generating circuit further comprises a third channel and a fourth channel for providing a third electrical-stimulation signal and a fourth electrical-stimulation signal, and the electrical-stimulation device further comprises:
 a fifth conductive member, connected to the fifth contact points;
 a sixth conductive member, connected to the sixth contact points;
 a seventh conductive member, connected to the seventh contact points; and
 an eighth conductive member, connected to the eighth contact points;
 wherein the fifth conductive member and the sixth conductive member are electrically connected to the third channel, so that the third electrical-stimulation signal is transmitted through the fifth contact points and the sixth contact points corresponding to the third channel;
 wherein the seventh conductive member and the eighth conductive member are electrically connected to the fourth channel, so that the fourth electrical-stimulation signal is transmitted through the seventh contact points and the eighth contact points corresponding to the fourth channel.

7. An electrical-stimulation system, comprising:
 at least one lead; and
 an electrical-stimulation device, electrically connected to the at least one lead, wherein the electrical-stimulation device comprises:
  an electrical-stimulation signal-generating circuit, having a first channel for providing a first electrical-stimulation signal;
  a first connection unit, having a plurality of first contact points and a plurality of second contact points, wherein the first contact points and the second contact points are alternately arranged;
  a first conductive member, connected to the first contact points; and
  a second conductive member, connected to the second contact points;
  wherein the first conductive member and the second conductive member are electrically connected to the first channel, so that the first electrical-stimulation signal is transmitted through the first contact points and the second contact points corresponding to the first channel.

8. The electrical-stimulation system as claimed in claim 7, wherein the lead has a plurality of first electrodes and a plurality of second electrodes alternately arranged, wherein the lead is coupled to the first connection unit, each of the first electrodes is correspondingly coupled to each of the first contact points, and each of the second electrodes is correspondingly coupled to each of the second contact points.

9. The electrical-stimulation system as claimed in claim 8, wherein a distance between the first electrode and the second electrode which are adjacent to each other is between 1 mm and 8 mm.

10. The electrical-stimulation system as claimed in claim 7, wherein the first electrical-stimulation signal is an alternating current signal, and a pulse frequency range thereof is between 0 and 1 KHz.

11. The electrical-stimulation system as claimed in claim 7, wherein an intra-pulse frequency range of the first electrical-stimulation signal is 100 KHz to 1000 KHz.

12. The electrical-stimulation system as claimed in claim 7, wherein electrical polarities of the first contact points and the second contact points are opposite.

13. An operation method of an electrical-stimulation device, comprising:
 providing a first electrical-stimulation signal via a first channel of an electrical-stimulation signal-generating circuit;
 providing a first connection unit, wherein the first connection unit has a plurality of first contact points and a plurality of second contact points, and the first contact points and the second contact points are alternately arranged;
 using a first conductive member to connect to the first contact points;
 using a second conductive member to connect to the second contact points;
 electrically connecting the first conductive member and the second conductive member to the first channel; and
 transmitting the first electrical-stimulation signal through the first contact points and the second contact points corresponding to the first channel.

14. The operation method of the electrical-stimulation device as claimed in claim 13, further comprising:
 providing a second electrical-stimulation signal via a second channel of the electrical-stimulation signal-generating circuit;
 providing a second connection unit, wherein the second connection unit has a plurality of third contact points and a plurality of fourth contact points, wherein the third contact points and the fourth contact points are alternately arranged;
 using a third conductive member to connect to the third contact points;
 using a fourth conductive member to connect to the fourth contact points;
 electrically connecting the third conductive member and the fourth conductive member to the second channel; and transmitting the second electrical-stimulation signal through the third contact points and the fourth contact points corresponding to the second channel.

15. The operation method of the electrical-stimulation device as claimed in claim 13, wherein the first electrical-stimulation signal is an alternating current signal, and a pulse frequency range thereof is between 0 and 1 KHz.

16. The operation method of the electrical-stimulation device as claimed in claim 13, wherein an intra-pulse frequency range of the first electrical-stimulation signal is 100 KHz to 1000 KHz.

17. The operation method of the electrical-stimulation device as claimed in claim 13, wherein the first connection unit further has a plurality of third contact points and a plurality of fourth contact points, the third contact points and the fourth contact points are alternately arranged, and the operation method further comprises:

providing a second electrical-stimulation signal via a second channel of the electrical-stimulation signal-generating circuit;

using a third conductive member to connect to the third contact points;

using a fourth conductive member to connect to the fourth contact points;

electrically connecting the third conductive member and the fourth conductive member to the second channel; and transmitting the second electrical-stimulation signal through the third contact points and the fourth contact points corresponding to the second channel.

18. The operation method of the electrical-stimulation device as claimed in claim 17, wherein a time difference exists between the first electrical-stimulation signal provided by the first channel and the second electrical-stimulation signal provided by the second channel.

19. The operation method of the electrical-stimulation device as claimed in claim 18, wherein the time difference is between 0 seconds and 2 seconds.

* * * * *